United States Patent
Hsiao et al.

(10) Patent No.: US 12,364,717 B2
(45) Date of Patent: *Jul. 22, 2025

(54) COMPOSITIONS AND METHODS FOR INHIBITING SEIZURES

(71) Applicant: The Regents of the University of California, Oakland, CA (US)

(72) Inventors: Elaine Hsiao, Los Angeles, CA (US); Jessica Yano, Los Angeles, CA (US); Helen Vuong, Los Angeles, CA (US); Christine Olson, Los Angeles, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/390,652

(22) Filed: Dec. 20, 2023

(65) Prior Publication Data

US 2024/0238350 A1 Jul. 18, 2024

Related U.S. Application Data

(60) Division of application No. 17/486,299, filed on Sep. 27, 2021, now Pat. No. 11,883,441, which is a continuation of application No. 16/471,460, filed as application No. PCT/US2017/067548 on Dec. 20, 2017, now Pat. No. 11,129,858.

(60) Provisional application No. 62/436,711, filed on Dec. 20, 2016, provisional application No. 62/447,992, filed on Jan. 19, 2017.

(51) Int. Cl.
| | |
|---|---|
| *A61K 35/741* | (2015.01) |
| *A23L 33/00* | (2016.01) |
| *A23L 33/135* | (2016.01) |
| *A61K 9/00* | (2006.01) |
| *A61K 35/00* | (2006.01) |
| *A61K 35/74* | (2015.01) |
| *A61K 39/02* | (2006.01) |
| *A61P 25/00* | (2006.01) |
| *A61P 25/08* | (2006.01) |

(52) U.S. Cl.
CPC ............ *A61K 35/74* (2013.01); *A23L 33/135* (2016.08); *A23L 33/30* (2016.08); *A61K 35/741* (2013.01); *A61K 39/0216* (2013.01); *A61P 25/00* (2018.01); *A61K 9/0031* (2013.01); *A61K 9/0053* (2013.01); *A61K 2035/115* (2013.01)

(58) Field of Classification Search
None
See application file for complete search history.

(56) References Cited

U.S. PATENT DOCUMENTS

| | | |
|---|---|---|
| 11,129,858 B2 | 9/2021 | Hsiao et al. |
| 2016/0143961 A1 | 5/2016 | Berry et al. |
| 2016/0143962 A1 | 5/2016 | Berry et al. |
| 2016/0339065 A1 | 11/2016 | Adams et al. |
| 2020/0384037 A1 | 12/2020 | Hsiao et al. |
| 2022/0184084 A1 | 6/2022 | Heaney et al. |
| 2022/0184144 A1 | 6/2022 | Hsiao et al. |

FOREIGN PATENT DOCUMENTS

| | | |
|---|---|---|
| CA | 2940226 A1 | 8/2014 |
| CN | 104726596 A | 6/2015 |
| CN | 104918626 A | 9/2015 |
| WO | WO-2014075745 A1 | 5/2014 |
| WO | WO-2016185469 A1 | 11/2016 |
| WO | WO-2018/119048 A1 | 6/2018 |

OTHER PUBLICATIONS

Dooling et al. Cell Host & Microbe 24: 3-5, 2018.*
Barrington, "Individual Variation in Diet Response: Health Effects of Dietary Interventions on Mice with Diverse Genetic Backgrounds," North Carolina State University, 164 pages, Dec. 31, 2015.
Extended European Search Report for EP Application No. 17882543.6 dated Jun. 25, 2020.
International Search Report and Written Opinion for International Application No. PCT/US2017/067548 dated Mar. 28, 2018.
Keshavarzian et al., "Colonic bacterial composition in Parkinson's disease," Mov Disord, 30(10):1351-1360 (2015).
Newell wt al., "Kttogenic diet modifies the gut microbiota in a murine model of autism spectrum disorder," Molecular Autism, 7(1):3 (2016).
Olson et al., "The gut microbiota mediates the anti-seizure effects of the ketogenic diet," Cell, 173(7): 1728-1741 (2018).
Sharon et al., "The central nervous system and the gut microbiome," Cell, 167(4):915-932 (2016).
Tremlett et al., "Gut microbiota in early pediatric multiple sclerosis: a case-control study," Eur J Neurol, 23(8):1308-1321 (2016).
Winek et al., "The gut microbiome as therapeutic target in central nervous system diseases: implications for stroke," Neurotherapeutics, 13(4):762-774 (2016).
Wu et al., "Intestinal microbiota as an alternative therapeutic target for epilepsy," The Canadian Journal of Infections Diseases & Medical Microbiology, 1-6 (2016).
Zhao et al., "Akkermansia muciniphila improves metabolic profiles by reducing inflammation in chow diet-fed mice," Journal of Molecular Endocrinology, 58(1):1-14 (2016).

* cited by examiner

*Primary Examiner* — S. Devi

(74) *Attorney, Agent, or Firm* — Foley Hoag LLP; David P. Halstead; Allison L. Gilder

(57) ABSTRACT

Provided herein are methods and compositions related to treating or preventing seizures. In some aspects, provided herein are methods of treating or preventing seizures in a subject by administering to the subject a composition comprising *Parabacteroides* and *Akkermansia* bacteria.

12 Claims, 44 Drawing Sheets

COMPOSITIONS AND METHODS FOR INHIBITING SEIZURES

RELATED APPLICATIONS

This application is a divisional application of U.S. application Ser. No. 17/486,299, filed on Sep. 27, 2021, now U.S. Pat. No. 11,883,441, which is a continuation application of U.S. application Ser. No. 16/471,460, filed on Jun. 19, 2019, now U.S. Pat. No. 11,129,858, which is a § 371 National Stage of International Application serial number PCT/US17/67548, filed on Dec. 20, 2017, which claims the benefit of priority to U.S. Provisional Patent Application Ser. No. 62/436,711, filed Dec. 20, 2016, and U.S. Provisional Patent Application Ser. No. 62/447,992 filed Jan. 19, 2017, each of which are herein incorporated by reference in their entireties.

GOVERNMENT SUPPORT

This invention was made with Government support under Grant Number GM065823 and Grant Number GM106996, awarded by the National Institutes of Health. The Government has certain rights in the invention.

BACKGROUND

Epilepsy is characterized by recurrent seizures that can lead to loss of awareness, loss of consciousness, and/or disturbances of movement, autonomic function, sensation (including vision, hearing and taste), mood, and/or mental function. Epilepsy afflicts 1-2% of the population in the developed world.

The low-carbohydrate, high-fat ketogenic diet (KD) is a treatment for refractory epilepsy, wherein more than one-third of epileptic individuals do not respond to existing anticonvulsant medications. The efficacy of the KD is supported by multiple retrospective and prospective studies, which estimate that ~30% of patients become seizure-free, and ~60% experience significant benefit. However, despite its value for treating epilepsy and its increasing application to other disorders, including autism, Alzheimer's disease, Parkinson's disease, metabolic syndrome and cancer, use of the KD remains low due to difficulties with implementation, dietary compliance and adverse side effects. In fact, even with successful seizure reduction, epileptic patient retention on the KD is only an estimated 12% by the third year of dietary therapy. Moreover, mechanisms underlying the beneficial effects of the KD are poorly understood, and molecular and/or cellular targets for intervention are lacking. That the diet succeeds in controlling various types of symptoms in cases when drugs fail suggests that it enhances endogenous neuroprotective pathways that are not targeted by existing medications.

SUMMARY

Provided herein are methods and compositions for mimicking the effects of a ketogenic diet by administering probiotic compositions to a subject. In certain embodiments, the methods and compositions are for the treatment or prevention of seizures in a subject (e.g., a subject with a neurodevelopmental disorder, such as autism spectrum disorder, Rett syndrome, fragile X, attention deficit disorder (ADD), attention deficit/hyperactivity disorder (ADHD), refractory epilepsy, and/or non-refractory epilepsy). In other embodiments, the methods and compositions are for preventing or treating a condition (e.g., epilepsy, seizures, autism spectrum disorder, Alzheimer's disease, Huntington's disease, Parkinson's disease, amyotrophic lateral sclerosis (ALS), cancer, stroke, a metabolic disease (e.g., diabetes or obesity), a mitochondrial disorder, depression, migraines (e.g., chronic migraines), Rett syndrome, attention deficit disorder, fragile X syndrome, or traumatic brain injury (TBI)) in a subject. Preferably, the methods comprise administering to the subject a composition comprising bacteria of the *Akkermansia* (Akk) and *Parabacteroides* (Pb) genera, or multiple compositions that together comprise bacteria of the *Akkermansia* (Akk) and *Parabacteroides* (Pb) genera. In some embodiments, the compositions comprise bacteria of the *Akkermansia* (Akk) and *Parabacteroides* (Pb) genera. In some embodiments, the bacteria of the *Akkermansia* (Akk) genus comprise *Akkermansia muciniphila*. In some embodiments, the bacteria of the *Parabacteroides* (Pb) genus comprise *Parabacteroides merdae* and/or *Parabacteroides distasonis*. In some aspects, the methods comprise depleting the gut microbiota of the subject and administering a composition comprising bacteria of *Akkermansia* genus (e.g., *Akkermansia muciniphila*) and *Parabacteroides* genus (e.g., *Parabacteroides merdae* or *Parabacteroides distasonis*) to the subject. In some embodiments, at least 10%, at least 30%, at least 50%, at least 70%, or at least 90% of the bacteria in the composition are *Akkermansia* (Akk) bacteria. In some embodiments, at least 10%, at least 30%, at least 50%, at least 70%, or at least 90% of the bacteria in the composition are *Parabacteroides* (Pb) bacteria. In some embodiments, the subject is on a diet, and the diet may be a control diet, a ketogenic diet, a high fat diet, or a low carbohydrate diet. The composition may be formulated for oral or rectal delivery. The composition may be a food product. In some embodiments, the food product is a dairy product (e.g., yogurt). In some embodiments, the composition comprises probiotics. In some embodiments, the composition is self-administered. In some embodiments, the composition comprises a fecal sample (e.g., a fecal sample from a fecal bank) comprising bacteria of the *Akkermansia* genus (e.g., *Akkermansia muciniphila*) and bacteria of the *Parabacteroides* (Pb) genus (e.g., *Parabacteroides merdae* or *Parabacteroides distasonis*). In some embodiments, the subject is given antibiotics to deplete the subject's gut microbiota.

BRIEF DESCRIPTION OF THE FIGURES

FIG. 1A shows seizure thresholds in response to 6-Hz stimulation in independent cohorts of mice fed the control diet (CD) or ketogenic diet (KD) for 2, 4, 8, 10 or 14 days (left). n=8, 6, 9, 20, 6 (CD); 8, 7, 12, 21, 5 (KD). Behavior in representative cohort of seizure-tested mice at 14 days post dietary treatment (right). Dashed line at y=10 seconds represents threshold for scoring seizures, and triangle at 24 mA denotes starting current per experimental cohort. n=16. FIG. 1B shows levels of serum glucose in independent cohorts of mice fed CD or KD for 2, 4, 8, 10 or 14 days. Data are normalized to serum glucose levels seen in SPF CD mice for each time point. n=8, 5, 8, 8, 19 (CD); 8, 8, 8, 7, 19 (KD). FIG. 1C shows levels of serum beta-hydroxybutyrate (BHB) in independent cohorts of mice fed CD or KD for 2, 4, 8, 10 or 14 days. n=8, 13, 8, 8, 37 (CD); 8, 16, 8, 7, 38 (KD). FIG. 1D shows Principal coordinates analysis (PCoA) of weighted (left) and unweighted (right) UniFrac distance matrices based on 16S rDNA profiling of feces from independent cohorts of mice fed CD or KD for 0, 4, 8 or 14 days. n=3 cages (9 mice)/group. FIG. 1E shows Alpha diversity of fecal 16S rDNA sequencing data from mice fed CD or KD for 14 days. n=3 cages/group. FIG. 1F shows the relative abundance of *Akkermansia miciniphila* and *Parabacteroides* spp. from fecal 16S rDNA sequencing data. n=3 cages (9 mice)/group. Data are presented as mean±s.e.m. Two-way ANOVA with Bonferroni (a-c, e), Kruskal-Wallis with Bonferroni (f): $P<0.05$, $P<0.01$, *$P<0.001$, ****$P<0.0001$. n.s.=not statistically significant. SPF=specific pathogen-free (conventionally-colonized), CD=control diet, KD=ketogenic diet, CC50=current intensity producing seizures in 50% of mice tested, BHB=beta-hydroxybutyrate, OTUs-operational taxonomic units.

FIG. 2A shows the Alpha diversity based on 16S rDNA sequencing of the fecal gut microbiota on days 0, 4, 8, and 14 after treatment with the CD (top) vs. KD (bottom) n=3 per time point. FIG. 2B shows the relative abundances of select bacterial taxa that are enriched in SPF mice fed KD (top row) or CD (bottom row). n=3. Data are presented as mean+s.e.m. Kruskal-Wallis with Bonferroni: *$P<0.05$, $P<0.01$, *$P<0.0001$. n.s.=not statistically significant. CD=control diet, KD=ketogenic diet.

FIG. 3A shows seizure thresholds in response to 6-Hz stimulation in SPF, GF or conventionalized GF mice fed CD or KD. n=13, 18, 12, 6. FIG. 3B shows serum BHB (left) and glucose (right) levels in SPF, GF or conventionalized GF mice fed CD or KD. n=37, 38, 19, 8. FIG. 3C shows seizure thresholds in response to 6-Hz stimulation in SPF mice treated with vehicle or Abx pre-dietary treatment. n=13, 18, 13. FIG. 3D shows serum BHB (left) and glucose (right) levels in SPF mice treated with vehicle or Abx pre-dietary treatment. n=18, 18, 19 (BHB); n=12, 11, 11 (glucose). Data are presented as mean+s.e.m. One-way ANOVA with Bonferroni: *$P<0.05$, $P<0.01$, *$P<0.001$, ****$P<0.0001$. n.s.=not statistically significant. SPF=specific pathogen-free (conventionally-colonized), GF=germ-free, GF-conv=germ-free conventionalized with SPF microbiota, CD=control diet, KD=ketogenic diet, CC50-current intensity producing seizures in 50% of mice tested. BHB-beta-hydroxybutyrate, veh=vehicle, Abx=antibiotics (ampicillin, vancomycin, neomycin, metronidazole [AVNM]).

FIG. 4A shows seizure thresholds in response to 6-Hz stimulation in SPF mice pre-treated with vehicle or Abx, and colonized with *Parabacteroides* spp. (*P. merdae* and *P. distasonis*), *Akkermansia muciniphila*, both, or *Bifidobacterium longum* (left). n=13, 18, 15, 6, 8, 5, 5. Behavior in representative cohort of seizure-tested mice (right). Dashed line at y=10 seconds represents the threshold for scoring seizures, and triangle at 24 mA denotes the starting current per experimental cohort. n=12, 16, 8, 25. FIG. 4B shows seizure thresholds in response to 6-Hz stimulation in GF mice colonized with *Parabacteroides* spp. (*P. merdae* and *P. distasonis*) and/or *Akkermansia muciniphila* (top). n=15, 4, 9, 9. Behavior in seizure-tested mice (bottom). Dashed line at y=10 seconds represents threshold for scoring seizures, and triangle at 24 mA denotes starting current per experimental cohort. n=17, 19. Data are presented as mean+s.e.m. One-way ANOVA with Bonferroni: $P<0.01$, *$P<0.001$, ****$P<0.0001$. SPF=specific pathogen-free (conventionally-colonized), GF=germ-free, CD=control diet, KD=ketogenic diet, CC50=current intensity producing seizures in 50% of mice tested, veh=vehicle, Abx-pre-treated with antibiotics (ampicillin, vancomycin, neomycin, metronidazole [AVNM]), Pb=*Parabacteroides* spp. (*P. merdae* and *P. distasonis*), Akk-*Akkermansia muciniphila*, AkkPb=*A. muciniphila, P. merdae* and *P. distasonis*, Bf=*Bifidobacterium longum*.

FIG. 5A shows the seizure thresholds in response to 6-Hz stimulation in Abx-treated SPF transplanted with the CD microbiota (CD-FMT) or KD microbiota (KD-FMT) and fed the CD or KD (left). n=6, 5, 5 Behavior in representative cohort of seizure-tested mice (right). Dashed line at y=10 seconds represents threshold for scoring seizures, and triangle at 24 mA denotes starting current per experimental cohort. n=12. FIG. 5B shows seizure thresholds in response to 6-Hz stimulation in SPF mice pre-treated with vehicle or Abx, and colonized with *Parabacteroides* spp. (*P. merdae* and *P. distasonis*), *Akkermansia muciniphila*, both, or *Bifidobacterium longum* (left). n=13, 18, 9, 8, 6, 6. FIG. 5C shows the seizure thresholds in response to 6-Hz stimulation in SPF mice orally gavaged with *Akkermansia muciniphila, P. merdae* and *P. distasonis* (AkkPb), *A. muciniphila* alone (Akk), or heat-killed *Akkermansia muciniphila* and *Parabacteroides* spp (hk-AkkPb) (left). n=6, 6, 4, 3. Data are presented as mean±: s.e.m. One-way ANOVA with Bonferroni: *$P<0.05$, *$P<0.001$, **$P<0.0001$. SPF=specific pathogen-free (conventionally-colonized), CD=control diet, KD=ketogenic diet, CC50=current intensity producing seizures in 50% of mice tested, CD-FMT-transplanted with CD microbiota, KDFMT=transplanted with KD microbiota, veh=vehicle, Abx=pre-treated with antibiotics (ampicillin, vancomycin, neomycin, metronidazole [AVNM]), Pb=*Parabacteroides* spp (*P. merdae* and *P. distasonis*), Akk=*Akkermansia muciniphila*, AkkPb=*A. miciniphila, P. merdae* and *P. distasonis*, Bf=*Bifidobacterium longum*, hk-AkkPb=heat-killed *A. muciniphila, P. merdae* and *P. distasonis*.

FIG. 6A shows Principal coordinates analysis (PCoA) of weighted UniFrac distance matrices based on longitudinal 16S rDNA profiling of feces from SPF mice fed CD for 28 days (CD), mice fed KD for 28 days (KD), or mice fed KD for 14 days followed by CD for 14 days (KD-CD). n=3 cages/group. FIG. 6B shows seizure thresholds in response to 6-Hz stimulation in SPF mice fed CD for 28 days (CD), mice fed KD for 28 days (KD), or mice fed KD for 14 days followed by CD for 14 days (KD-CD) (left). n=4. FIG. 6C shows seizure thresholds in response to 6-Hz stimulation in SPF mice at 21 days after probiotic treatment with *Akkermansia muciniphila, P. merdae* and *P. distasonis* (AkkPb), *A. muciniphila* alone (Akk), or heat-killed *Akkermansia muciniphila* and *Parabacteroides* spp (hk-AkkPb). (left). n=8. FIG. 6D shows seizure thresholds in response to 6-Hz stimulation in SPF mice orally gavaged for 4 days with vehicle or *Akkermansia muciniphila, P. merdae* and *P. distasonis* (AkkPb). n=6, 7, 7, 7. Data are presented as mean+s.e.m. One-way ANOVA with Bonferroni: *$P<0.05$, $P<0.01$, **$P<0.0001$, n.s.=not statistically significant. SPF=specific pathogen-free (conventionally colonized), CD=control diet, KD=ketogenic diet, KD-CD=fed KD for 14 days followed by CD for 14 days. CC50-current intensity producing seizures in 50% of mice tested, veh=vehicle, Akk=*Akkermansia muciniphila*, AkkPb=*A. miciniphila, P.*

*merdae* and *P. distasonis*, hk-AkkPb=heat-killed *A. muciniphila, P. merdae* and *P. distasonis*.

Figure 7A:
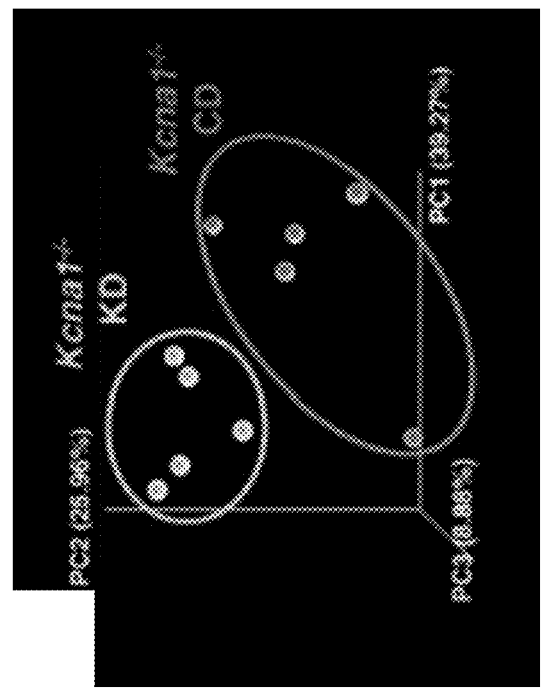
Figure 7B:
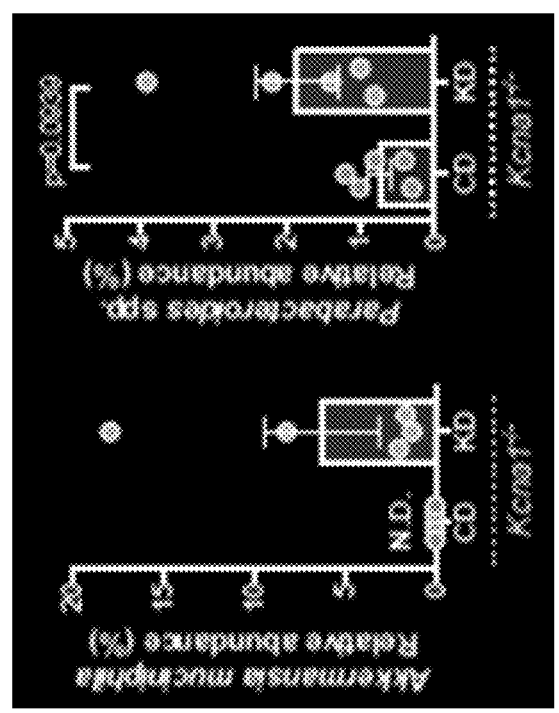
Figure 7C:
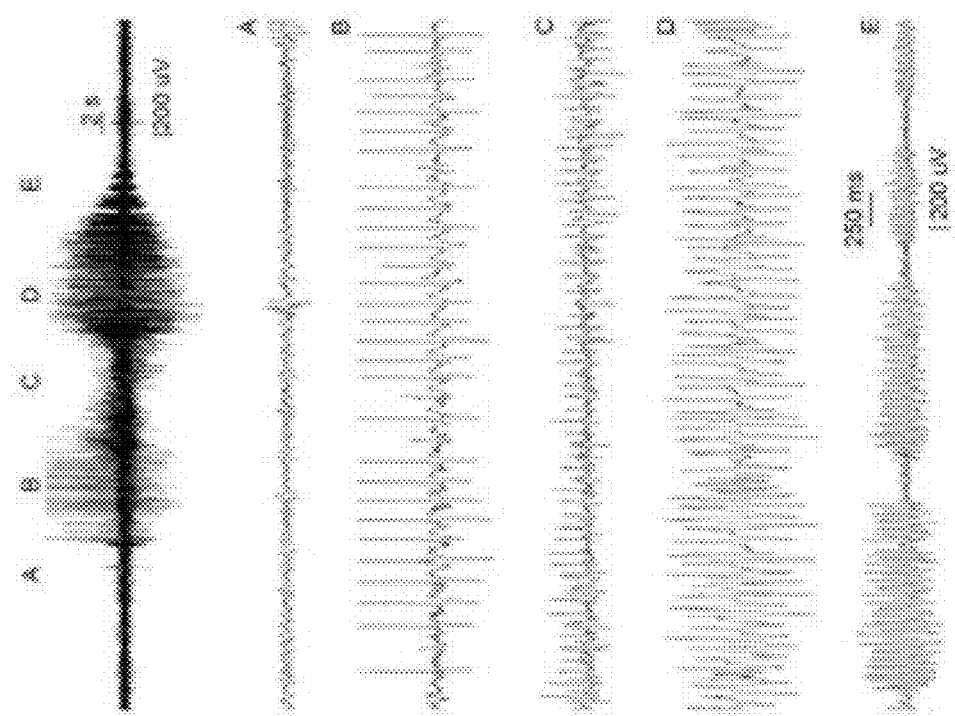
Figure 7D:
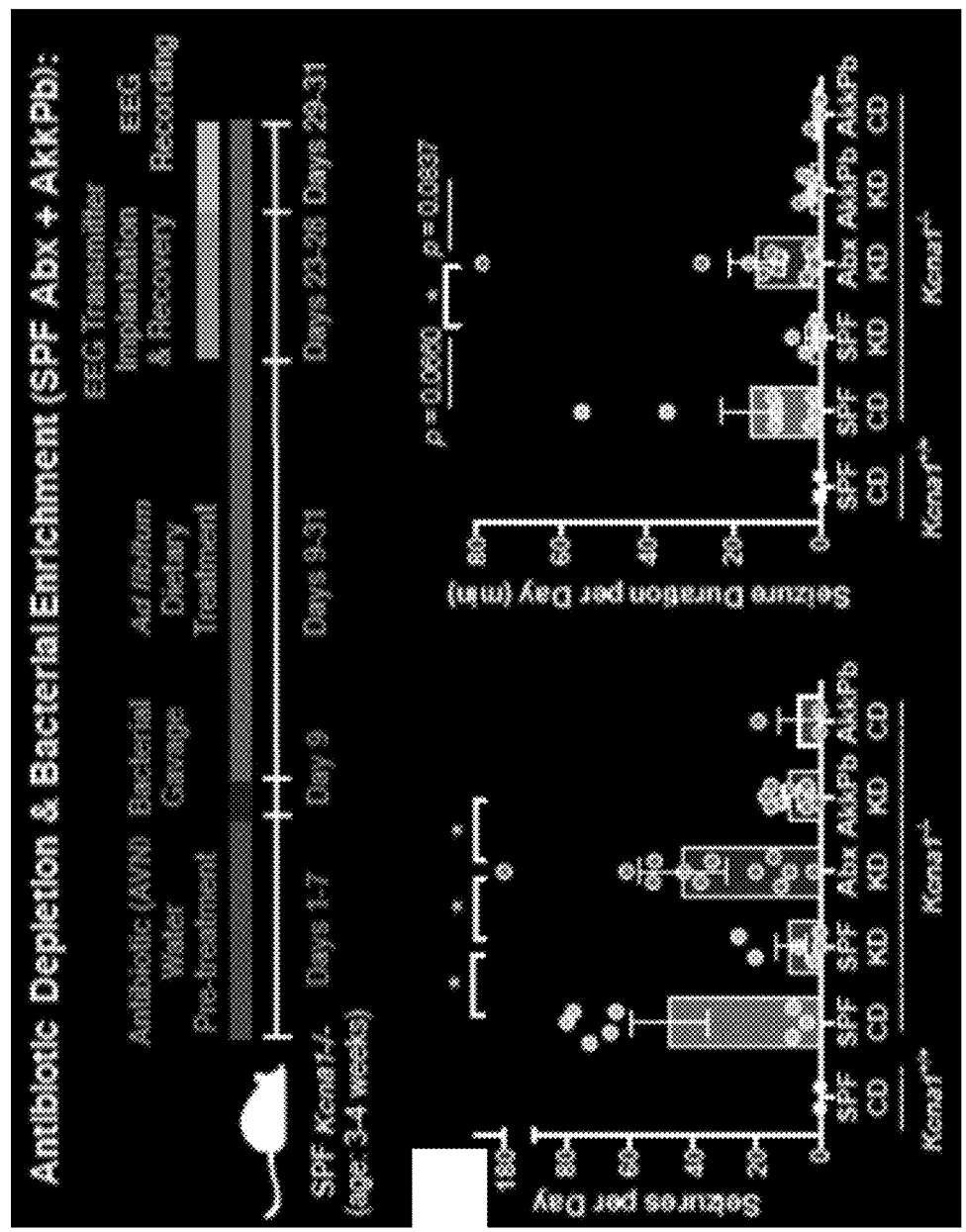
Figure 7E:
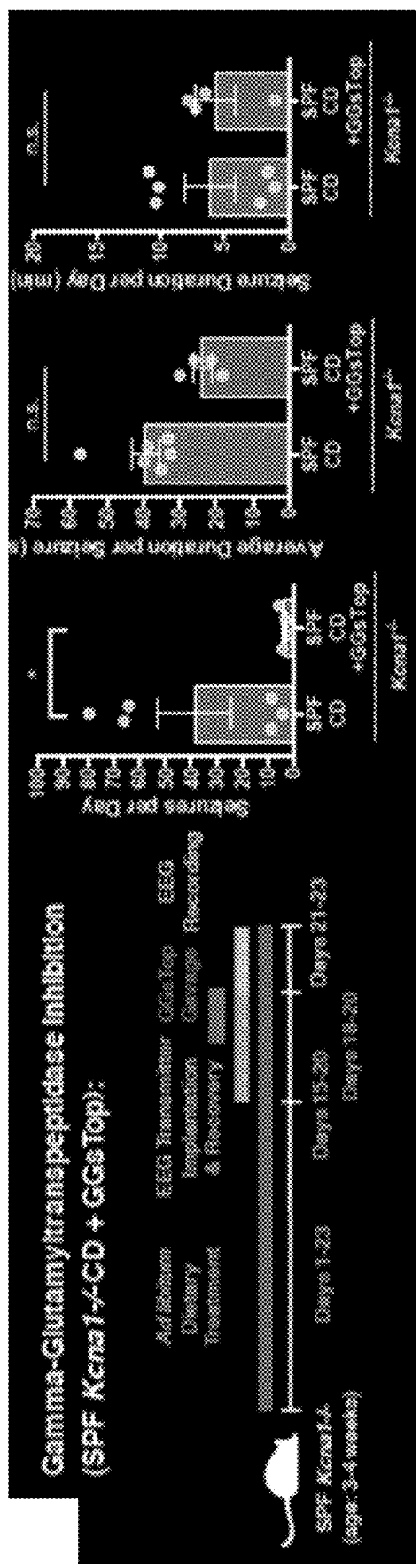

FIGS. 7A-E show KD-associated bacteria mediate protection against Tonic-Clonic seizures in response to a ketogenic diet. FIG. 7A shows the Principal coordinates analysis (PCoA) of weighted UniFrac distances based on 16S rDNA profiling of feces Kcna1−/− mice fed CD or KD for 14 days. n=5 cages/group. FIG. 7B shows the relative abundances of *Akkermansia muciniphila* and *Parabacteroides* spp. from fecal 16S rDNA sequencing data (right). n=5 cages/group. FIG. 7C shows representative EEG trace showing stages used to define seizures quantified in FIG. 7D. FIG. 7D shows the average number of seizures per day (left) and total duration of seizures per day (right) in SPF Kcna1−/− mice treated with vehicle or Abx, colonized with *A. muciniphila* and *Parabacteroides* spp. or nothing, and fed CD or KD. n=2, 8, 6, 12, 9, 3. FIG. 7E shows the average number of seizures per day (left), average duration per seizure (middle) and total duration of seizures per day (right) in SPF CD Kcna1$^{-/-}$ mice treated with GGsTop. Data for SPF CD mice are as in (D). n=6, 4. Data are presented as mean±s.e.m. Kruskal-Wallis with Bonferroni (A, B), non-parametric one-way nested ANOVA with Dunn (D), non-parametric Kolgomorov-Smirnov t test (E). SPF=specific pathogen-free (conventionally-colonized), CD=control diet, KD=ketogenic diet, veh=vehicle, Abx=pre-treated with antibiotics (ampicillin, vancomycin, neomycin, metronidazole [AVNM]), AkkPb=*A. muciniphila, P. merdae* and *P. distasonis*.

Figure 8A:
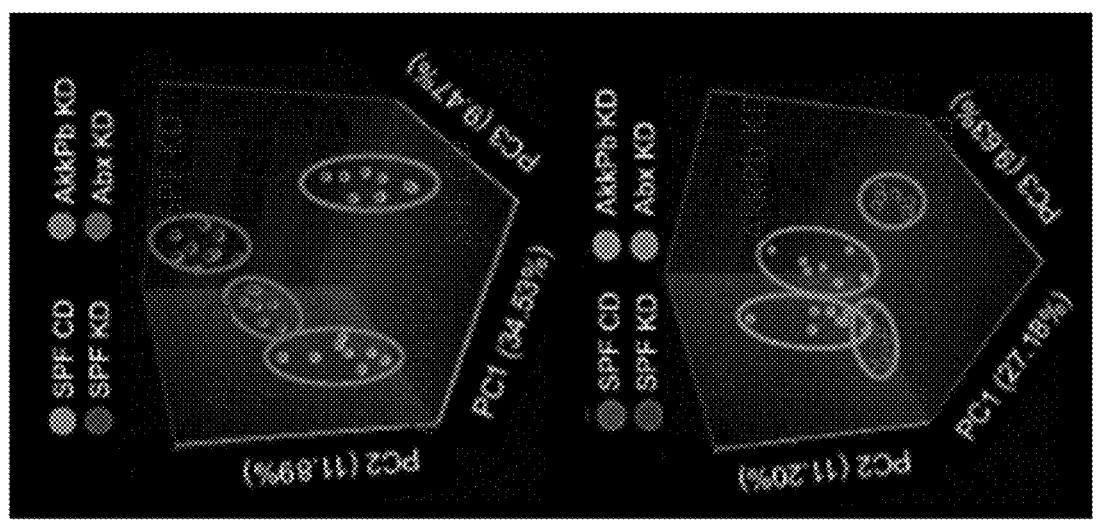
Figure 8B:
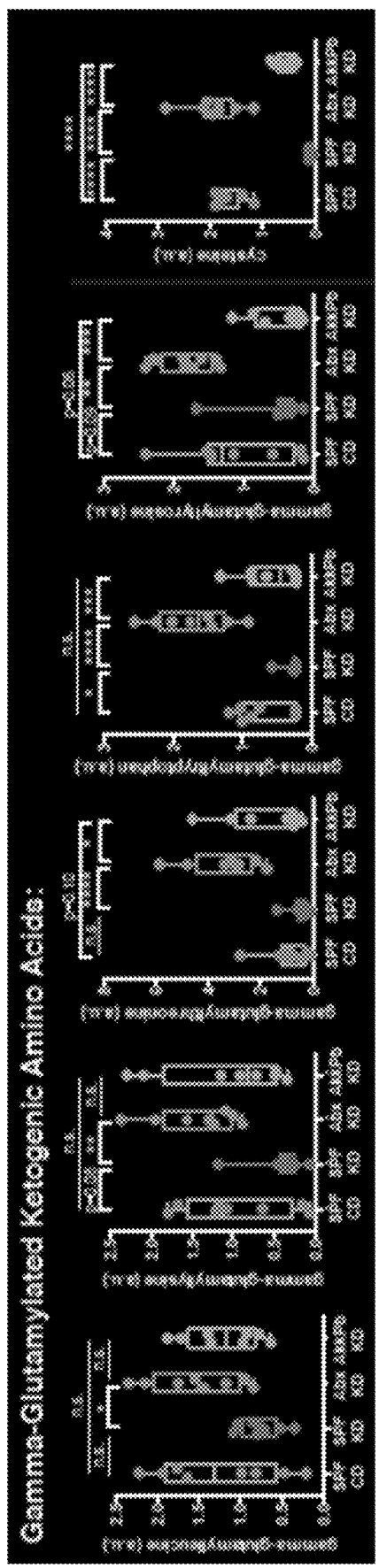
Figure 8C:
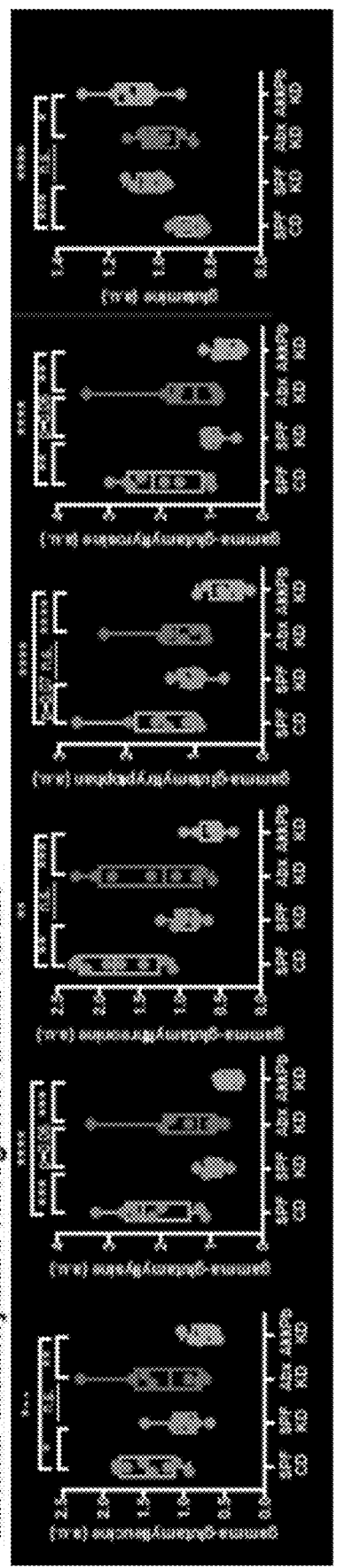
Figure 8D:
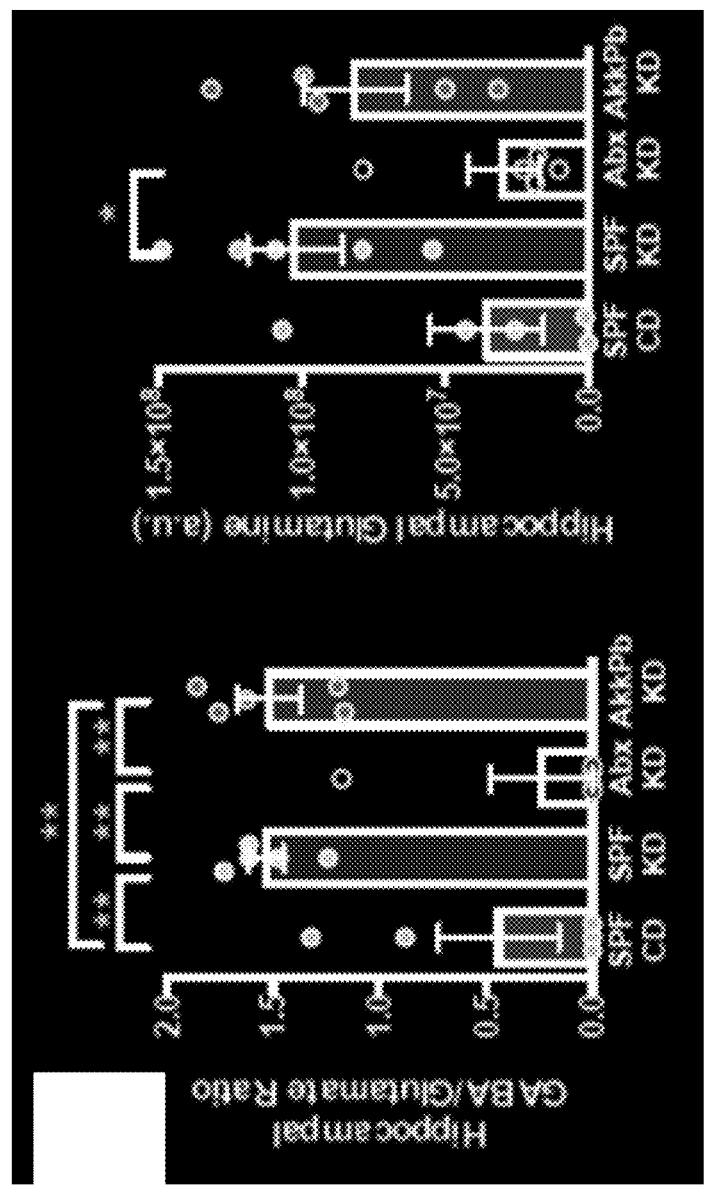

FIGS. 8A-D show the association of the reductions in peripheral gamma-glutamyl amino acids and increases in hippocampal GABA/Glutamate ratios with diet and microbiota-dependent seizure protection. FIG. 8A shows principal components analysis of colonic lumenal metabolites (top) and serum metabolites (bottom) from SPF mice fed CD, SPF mice fed KD, Abx-treated mice fed KD, and AkkPb-colonized mice fed KD. n=8 cages/group. FIG. 8B shows the levels of gamma-glutamylated amino acids and cysteine in colonic lumenal contents from SPF mice fed CD, SPF mice fed KD, Abx-treated mice fed KD, and AkkPb-colonized mice fed KD. n=8 cages/group. FIG. 8C shows the levels of gamma-glutamyl amino acids and glutamine in sera from SPF mice fed CD, SPF mice fed KD, Abx-treated mice fed KD, and AkkPb-colonized mice fed KD. n=8 cages/group. FIG. 8D shows the Levels of GABA/glutamate (left) and glutamine (right) in hippocampi of SPF mice fed CD, SPF mice fed KD, Abx-treated mice fed KD, and AkkPb-colonized mice fed KD. n=5. Data are presented as mean+s.e.m. Two-way ANOVA contrasts (A-C), One-way ANOVA with Bonferroni (D): *$P<0.05$, $P<0.01$, *$P<0.001$, ****$P<0.0001$. n.s.=not statistically significant. CD=control diet, KD=ketogenic diet, SPF=specific pathogen-free (conventionally-colonized), veh=vehicle, Abx=pre-treated with antibiotics (ampicillin, vancomycin, neomycin, metronidazole [AVNM]), AkkPb=*A. muciniphila, P. merdae* and *P. distasonis*, a.u.=arbitrary units.

Figure 9A:
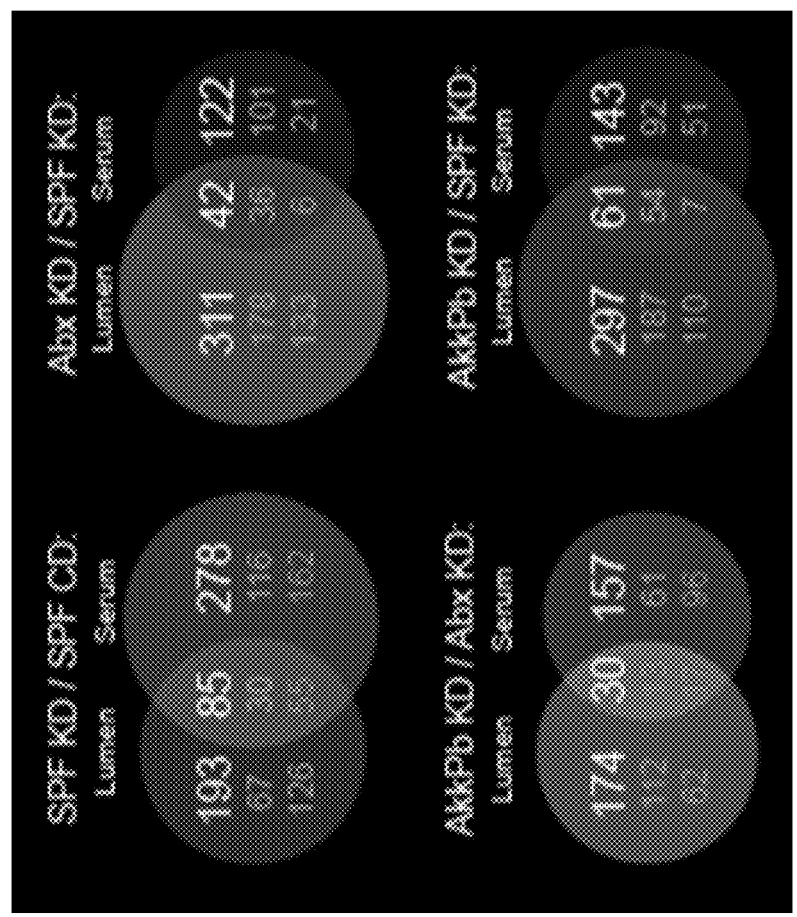
Figure 9B:
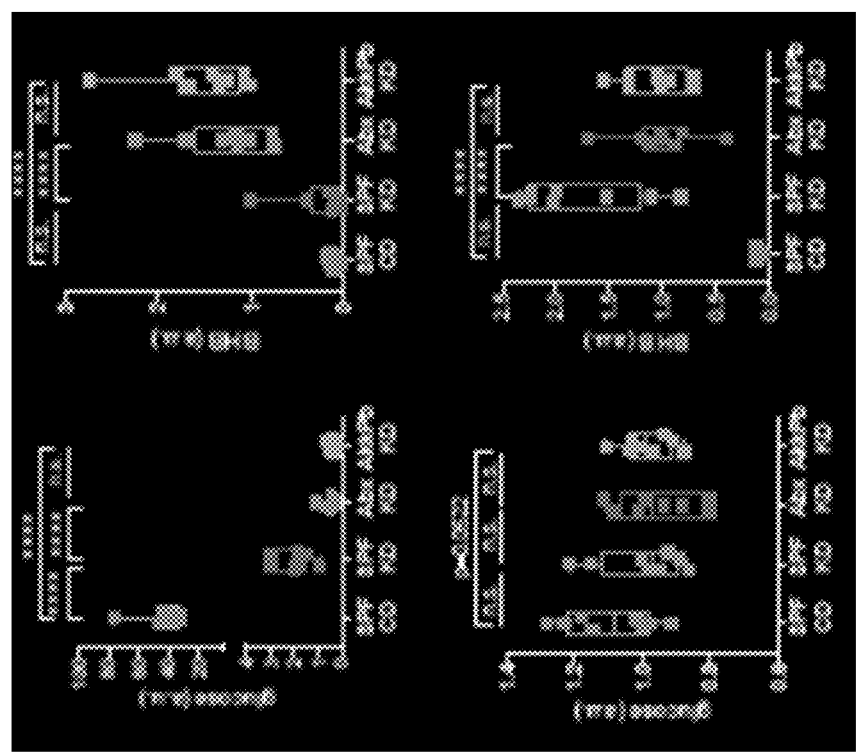
Figure 9C:
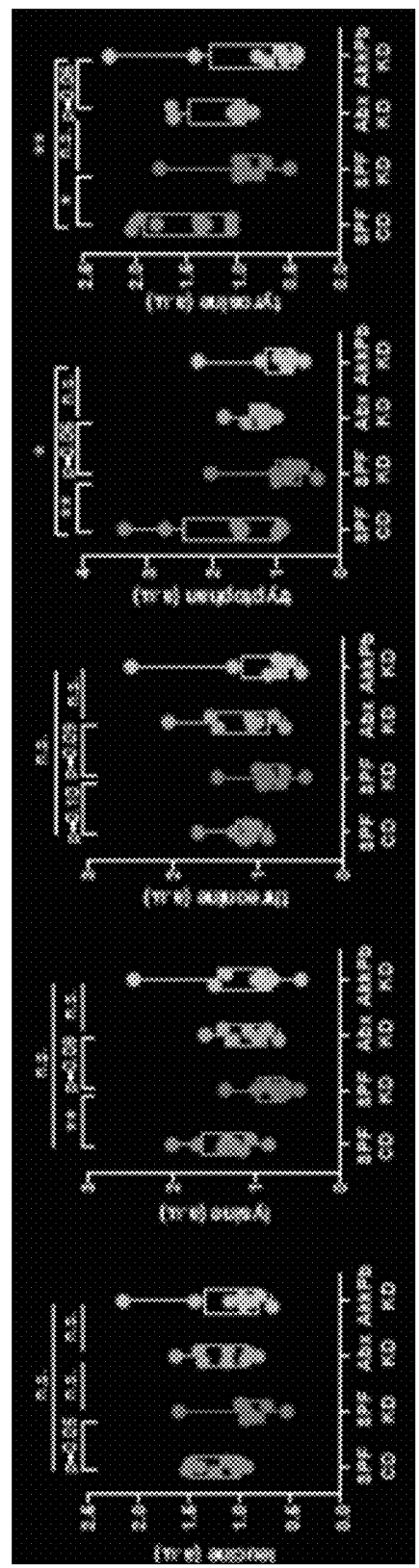
Figure 9D:
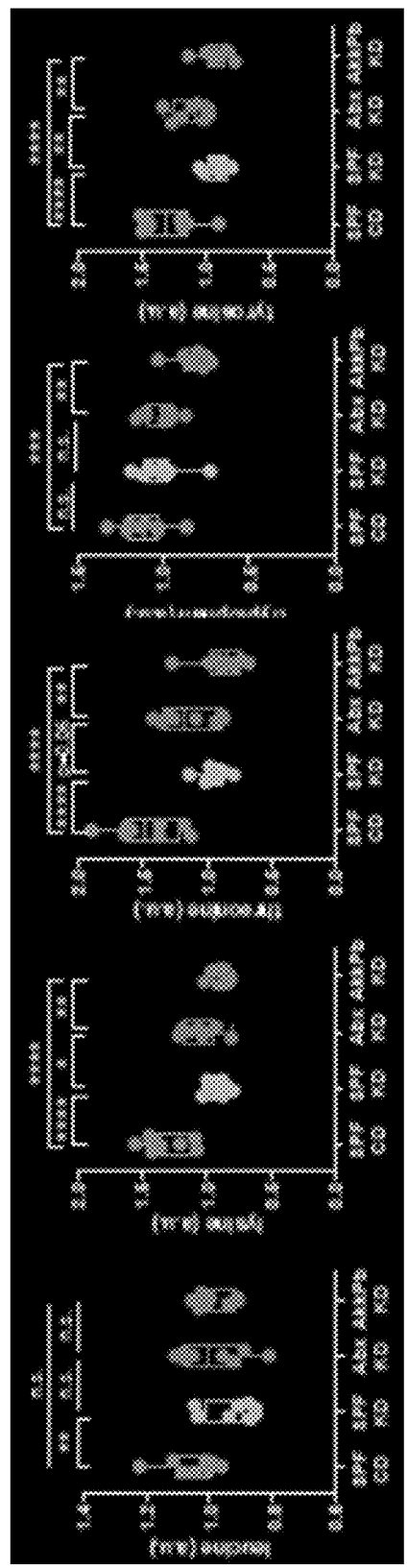

FIGS. 9A-D show the modulation of the colonic lumenal and serum metabolomes by the ketogenic diet and microbiota status. FIG. 9A shows the number of statistically significant alterations in metabolites out of the 622 detected in colonic lumen and 670 detected in serum. Values noted in black text are total number of metabolites altered, with values in green denoting upregulation and values in red denoting downregulation. n=8 cages/group. FIG. 9B shows the levels of glucose (left) and BHB (right) detected by metabolomics screening of colonic lumen (top) and serum (bottom). n=8 cages/group. FIG. 9C shows the levels of non-gamma glutamylated amino acids in colonic lumenal contents from SPF mice fed CD, SPF mice fed KD, Abx-treated mice fed KD, and AkkPb-colonized mice fed KD. n=8 cages/group. FIG. 9D shows the levels of non-gamma glutamylated amino acids in sera from SPF mice fed CD, SPF mice fed KD, Abx-treated mice fed KD, and AkkPb-colonized mice fed KD. n=8 cages/group. Data are presented as mean+s.e.m. Two-way ANOVA contrasts: *$P<0.05$, $P<0.01$, *$P<0.001$, ****$P<0.0001$. n.s.=not statistically significant. CD=control diet, KD=ketogenic diet, SPF=specific pathogen-free (conventionally-colonized), veh=vehicle, Abx=pre-treated with antibiotics (ampicillin, vancomycin, neomycin, metronidazole [AVNM]), AkkPb=*A. muciniphila, P. merdae* and *P. distasonis*, a.u.=arbitrary units, BHB-beta-hydroxybutyrate.

Figure 10A:
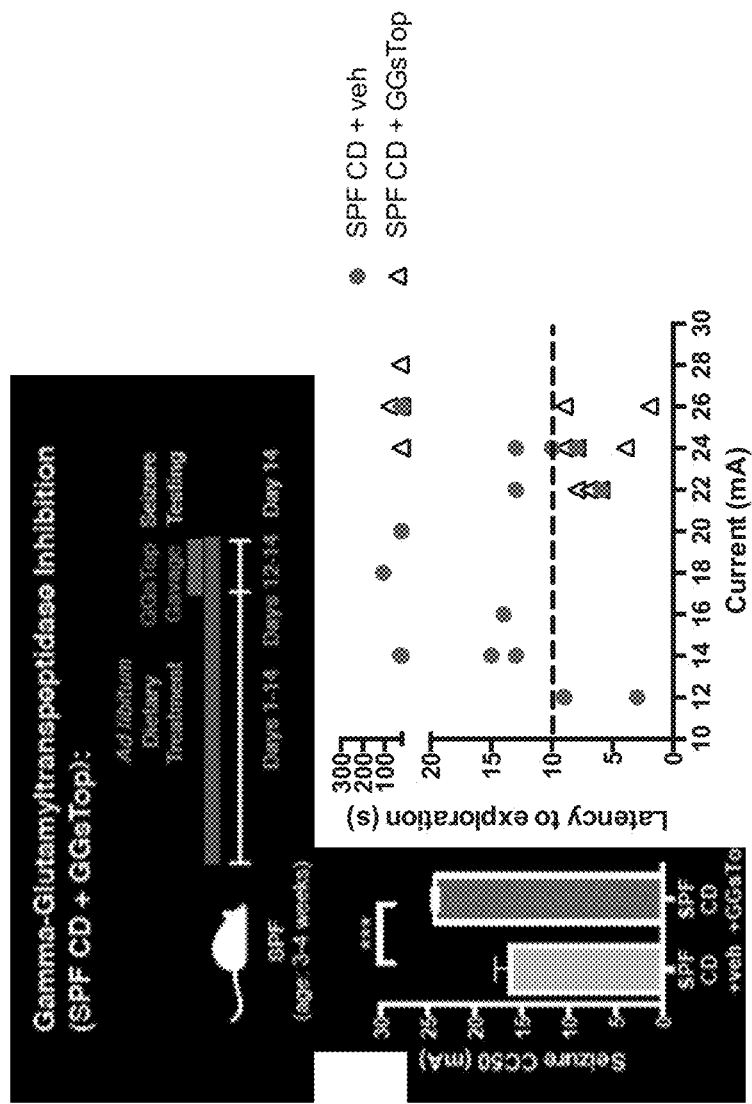
Figure 10B:
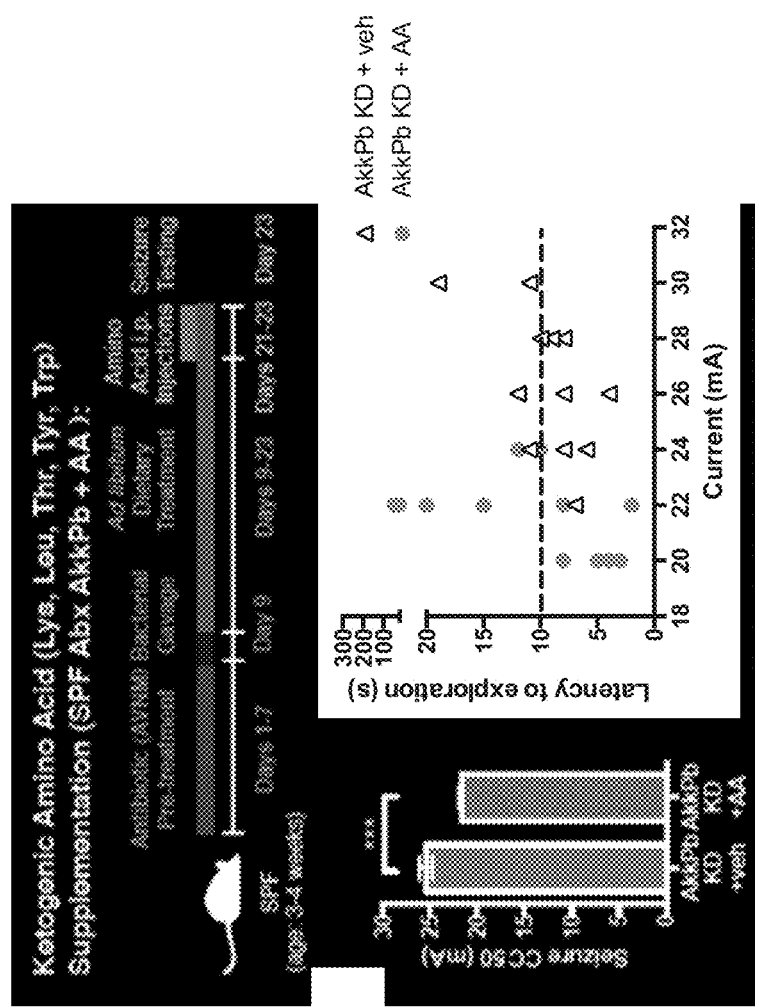
Figure 10C:
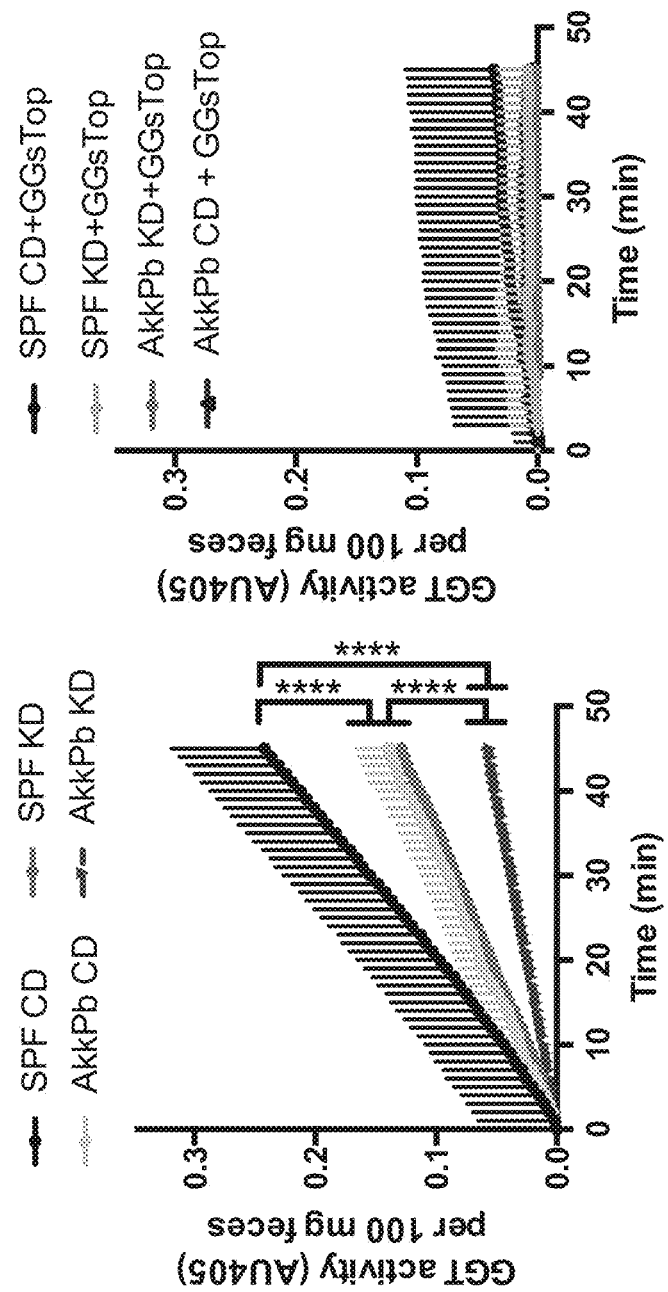
Figure 10D:
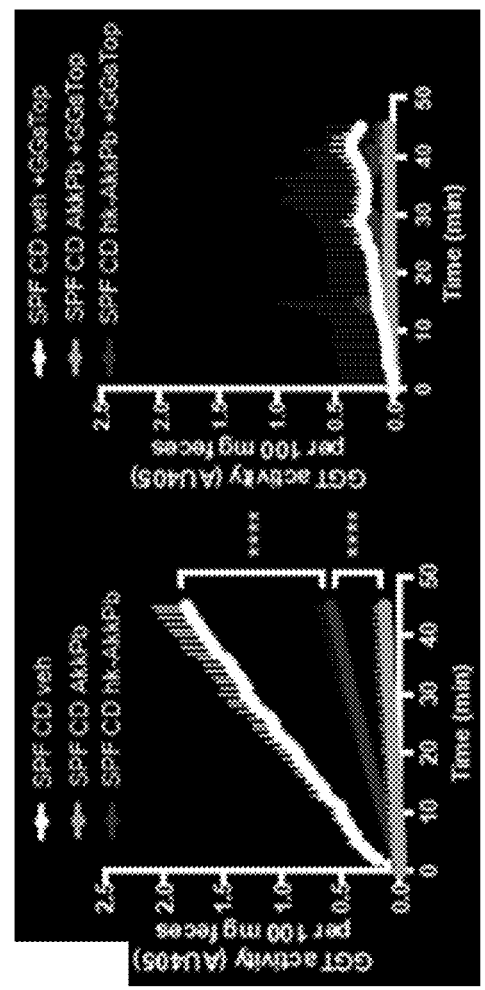
Figure 10E:
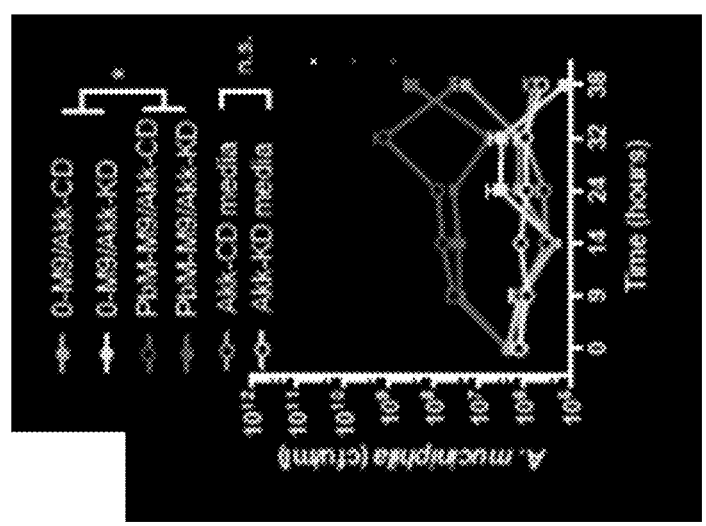
Figure 10F:
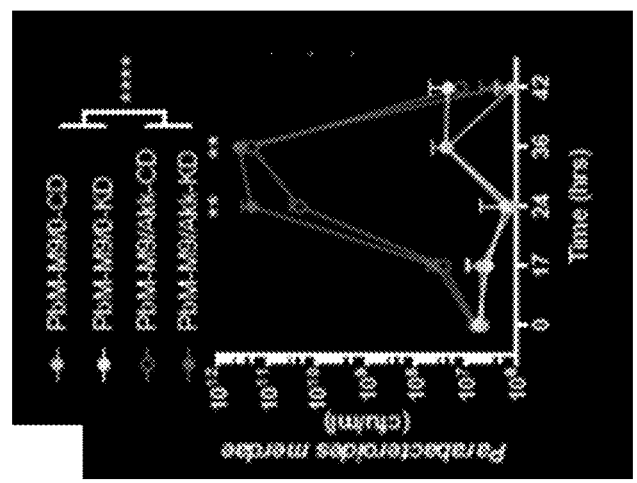
Figure 10G:
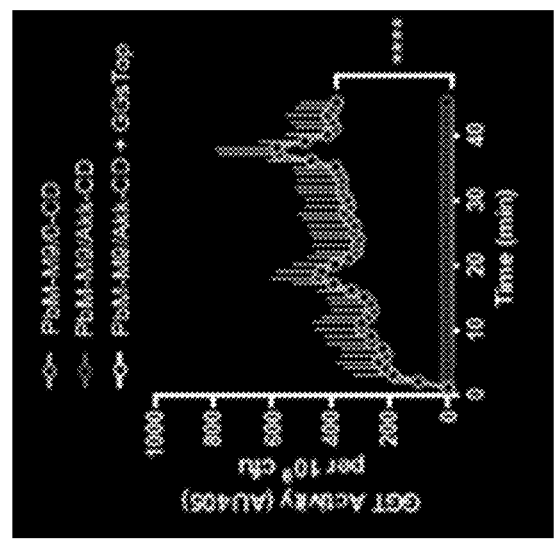
Figure 10H:
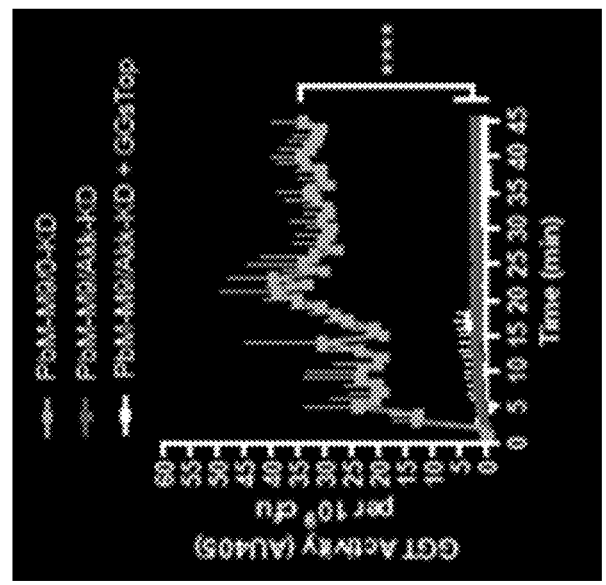

FIGS. 10A-H show that the ketogenic diet and bacterial cross-feeding reduces gamma-glutamyltranspeptidase (GGT) activity, which sufficiently confers seizure protection. FIG. 10A shows the 6-Hz seizure thresholds in response to oral gavage with the GGT inhibitor, GGsTop, in SPF mice fed CD (left). N=6, 9. Behavior in seizure-tested mice (right). Dashed line at y=10 seconds represents threshold for scoring seizures, and triangle at 24 mA denotes starting current per experimental cohort. n=16. FIG. 10B shows the 6-Hz seizure thresholds in response to supplementation with ketogenic amino acids in Abx-treated SPF mice enriched for *A. miciniphila* and *Parabacteroides* spp (left). n=5, 6. Behavior in seizure-tested mice (right). Dashed line at y=10 seconds represents threshold for scoring seizures, and triangle at 24 mA denotes starting current per experimental cohort. n=12. FIG. 10C shows the total GGT activity per 100 mg feces from SPF CD, SPF KD, AkkPb KD, or AkkPb CD mice (left), and inhibition by GGsTop (right). n=5. FIG. 10D shows the total GGT activity per 100 mg feces from SPF CD animals treated with vehicle, *A. muciniphila* and *Parabacteroides* spp. probiotic, or heat-killed bacteria for bi-daily for 28 days (left), and inhibition by GGsTop (right). n=5. FIG. 10E shows the levels of live *A. muciniphila* (Akk) after incubation in CD vs KD culture media or in CD or KD agar overlaid with M9 minimal media containing live *Parabacteroides merdae* (PbM) or no bacteria (0). n=3. FIG. 10F shows the levels of live PbM after incubation in M9 minimal media overlaid on CD or KD agar containing Akk or no bacteria (0). n=5. FIG. 10G shows GGT activity in *P. merdae* grown in M9 media overlaid on CD agar containing *A. muciniphila* or no bacteria at t=24 hrs, and inhibition of GGT activity by GGsTop. n=5. FIG. 10H shows GGT activity in *P. merdae* grown in M9 media overlaid on KD agar containing *A. muciniphila* or no bacteria at t=24 hrs, and inhibition of GGT activity by GGsTop. n=5. Data are presented as mean±s.e.m. Students't-test (a,b), Two-way ANOVA with Bonferroni (C, D), One-way ANOVA with Bonferroni (E-H): $P<0.01$, *$P<0.001$, ****$P<0.0001$. SPF=specific pathogen-free (conventionally-colonized), CD=control diet, KD=ketogenic diet, CC50=current intensity producing seizures in 50% of mice tested, AA=amino acids, veh=vehicle, Abx=pre-treated with antibiotics (ampicillin, vancomycin, neomycin, metronidazole [AVNM]), AkkPb=*A. muciniphila, P. merdae* and *P. distasonis*, GGsTop=GGT inhibitor, PbM=*Parabacteroides merdae*, Akk=*Akkermansia muciniphila*, M9=minimal media, GGT=gamma-glutamyltranspeptidase, AU=absorbance units.

Figure 11A:
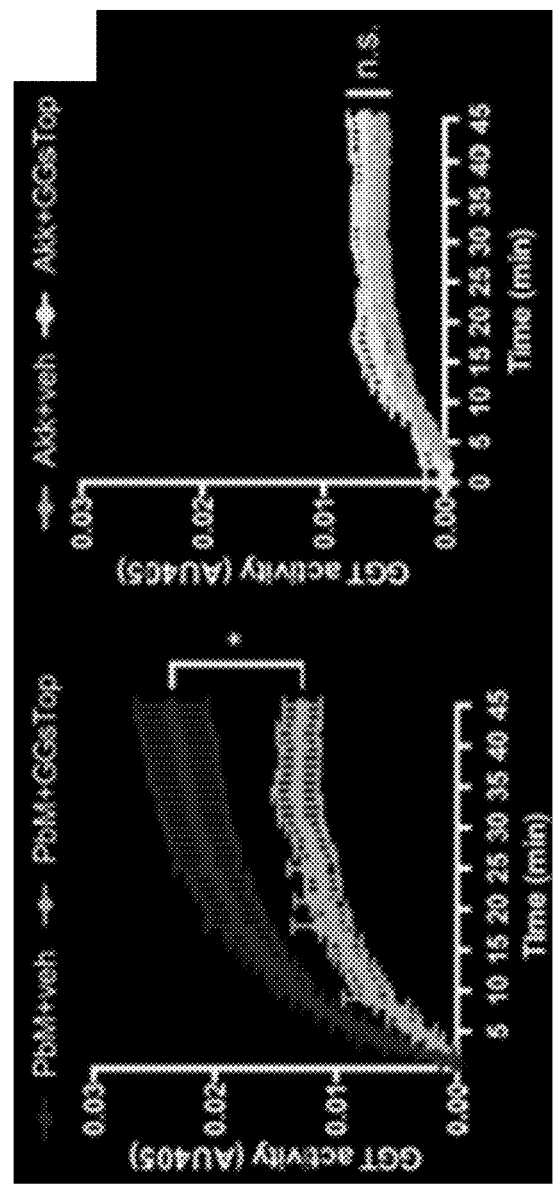

FIGS. 11A and B show the amino acid effects on seizures, bacterial GGT activity and dietary modulation of bacterial genes for amino acid metabolism. FIG. 11A shows GGT activity in conventionally-cultured *Parabacteroides merdae*

Figure 11B:
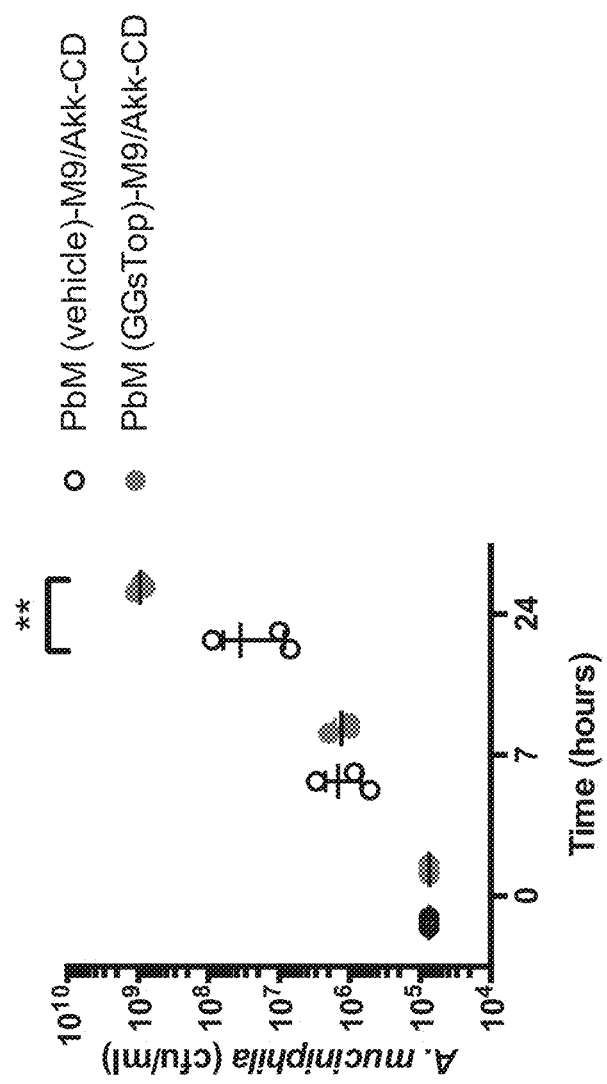

(left) and *A. muciniphila* (right), treated with GGsTop or vehicle. n=5. FIG. 11B shows the levels of *A. muciniphila* (Akk) after 0, 7, or 24 hours incubation in CD agar overlaid with *P. merdae* (PbM) that was pre-treated with vehicle or GGsTop in M9 minimal media. n=3. Data are presented as mean+s.e.m. One-way ANOVA with Bonferroni (a): *P<0.05, Two-way ANOVA with Bonferroni (b): **P<0.01, PbM=*Parabacteroides merdae*, Akk=*Akkermansia muciniphila*, GGsTop=GGT inhibitor, GGT=gamma-glutamyl-transpeptidase, AU=absorbance units.

DETAILED DESCRIPTION

Provided herein are methods and compositions for mimicking the effects of a ketogenic diet by administering probiotic compositions. In certain embodiments, the methods and compositions are for the treatment or prevention of seizures in a subject (e.g., a subject with a neurodevelopmental disorder, such as an autism spectrum disorder, Rett syndrome, fragile X, attention deficit disorder (ADD), attention-deficit/hyperactivity disorder (ADHD), refractory epilepsy, and/or non-refractory epilepsy). In other embodiments, the methods and compositions are for preventing or treating a condition (e.g., autism spectrum disorder, epilepsy, seizures, Alzheimer's disease, Huntington's disease, Parkinson's disease, amyotrophic lateral sclerosis (ALS), cancer, stroke, a metabolic disease (e.g., obesity or diabetes), a mitochondrial disorder, depression, migraines (e.g., chronic migraines), Rett syndrome, attention deficit disorder, fragile X syndrome, or traumatic brain injury (TBI)) in a subject. In preferred embodiments, the methods comprise administering to the subject a composition comprising bacteria of *Akkermansia* genus (e.g., *Akkermansia muciniphila*) and *Parabacteroides* genus (e.g., *Parabacteroides merdae* or *Parabacteroides distasonis*), or multiple compositions that together comprise bacteria of *Akkermansia* genus (e.g., *Akkermansia muciniphila*) and *Parabacteroides* genus (e.g., *Parabacteroides merdae* or *Parabacteroides distasonis*). In other embodiments, the methods and compositions alter neurotransmitter biosynthesis in a subject. In certain embodiments, the methods and compositions alter serum ketogenic amino acids in a subject. In other embodiments, the methods and compositions decrease gamma-glutamyl-transpeptidase activity in a subject. In certain embodiments, the methods and compositions decrease glutamine synthase activity in a subject. In other embodiments, the methods and compositions decrease gamma-glutamyl amino acids in a subject. In certain embodiments, the methods and compositions increase GABA/glutamate ratio levels in a subject. In other embodiments, the methods and compositions increase glutamine levels in a subject. In other embodiments, the methods comprise depleting the gut microbiota of the subject and administering a composition comprising bacteria of *Akkermansia* and *Parabacteroides* genera to the subject, or multiple compositions that together comprise bacteria of *Akkermansia* and *Parabacteroides* genera.

Definitions

As used herein in the specification, "a" or "an" may mean one or more. As used herein in the claim(s), when used in conjunction with the word "comprising", the words "a" or "an" may mean one or more than one. As used herein "another" may mean at least a second or more.

The phrase "pharmaceutically-acceptable carrier" as used herein means a pharmaceutically-acceptable material, composition or vehicle, such as a liquid or solid filler, diluent, excipient, solvent or encapsulating material. Each carrier must be "acceptable" in the sense of being compatible with the other ingredients of the formulation and not injurious to the subject. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

The term "preventing" is art-recognized, and when used in relation to a condition, such as a local recurrence, is well understood in the art, and includes administration of a composition which reduces the frequency of, or delays the onset of, symptoms of a medical condition in a subject relative to a subject which does not receive the composition. Thus, prevention of seizures includes, for example, reducing the number of seizures in a population of patients receiving a prophylactic treatment relative to an untreated control population, and/or delaying the appearance of detectable lesions in a treated population versus an untreated control population, e.g., by a statistically and/or clinically significant amount.

The term "prophylactic" or "therapeutic" treatment is art-recognized and includes administration to the host of one or more of the subject compositions. If it is administered prior to clinical manifestation of the unwanted condition (e.g., disease or other unwanted state of the host animal) then the treatment is prophylactic (i.e., it protects the host against developing the unwanted condition), whereas if it is administered after manifestation of the unwanted condition, the treatment is therapeutic (i.e., it is intended to diminish, ameliorate, or stabilize the existing unwanted condition or side effects thereof).

The term "subject" refers to a mammal, including, but not limited to, a human or non-human mammal, such as a bovine, equine, canine, ovine, or feline.

A "therapeutically effective amount" of a compound with respect to the subject method of treatment refers to an amount of the compound(s) in a preparation which, when administered as part of a desired dosage regimen (to a mammal, preferably a human) alleviates a symptom, ameliorates a condition, or slows the onset of disease conditions according to clinically acceptable standards for the disorder or condition to be treated or the cosmetic purpose, e.g., at a reasonable benefit/risk ratio applicable to any medical treatment.

As used herein, the term "treating" or "treatment" includes reversing, reducing, or arresting the symptoms, clinical signs, and underlying pathology of a condition in a manner to improve or stabilize a subject's condition.

Therapeutic Methods

The disclosure herein, relates, in part, to the discovery that the ketogenic diet (KD) induces substantial changes in the gut microbiome, and that enriching KD-associated bacteria via probiotic administration, fecal transplant, or selective microbial reconstitution of the native microbiome mimics the beneficial effects of the KD. Provided herein are methods and compositions that can replace the KD diet in the treatment or prevention of a condition as described. The methods and compositions described herein can be used separately or in conjunction with the KD diet in the treatment or prevention of a condition described herein.

In certain embodiments, the methods treat or prevent seizures in a subject. In some embodiments, the methods comprise administering a composition comprising bacteria of *Akkermansia* and *Parabacteroides* genera. In other embodiments, the methods alter neurotransmitter biosynthesis in a subject. In certain embodiments, the methods alter serum ketogenic amino acids in a subject. In other embodiments, the methods decrease gamma-glutamyltranspeptidase activity in a subject. In certain embodiments, the methods decrease glutamine synthase activity in a subject. In other embodiments, the methods decrease gamma-glutamyl amino acids in a subject. In certain embodiments, the methods increase GABA/glutamate ratio levels in a subject. In other embodiments, the methods increase glutamine levels in a subject. In other embodiments, the methods provided herein comprise depleting the gut microbiota of the subject and administering a composition comprising bacteria of *Akkermansia* genus (e.g., *Akkermansia muciniphila*) and *Parabacteroides* genus (e.g., *Parabacteroides merdae* or *Parabacteroides distasonis*) to the subject. In some embodiments, the subject has epilepsy (e.g., refractory or non-refractory epilepsy). In some embodiments, the subject has a neurodevelopmental disorder. Representative neurodevelopmental disorders include autism spectrum disorder, Rett syndrome, fragile X, attention deficit disorder, and attention-deficit/hyperactivity disorder. In some embodiments, the neurodevelopmental disorder is a disorder known to be comorbid with seizures.

In other embodiments, the subject has a condition responsive to a ketogenic diet. The condition may be Alzheimer's disease, Huntington's disease, Parkinson's disease, amyotrophic lateral sclerosis (ALS), cancer, stroke, a metabolic disease, a mitochondrial disorder, depression, migraines (e.g., chronic migraines), or traumatic brain injury (TBI). In some embodiments, the methods and compositions comprise administering to the subject a composition provided herein. In some embodiments, the condition is epilepsy, seizures, autism spectrum disorder, Alzheimer's disease, Huntington's disease, Parkinson's disease, amyotrophic lateral sclerosis (ALS), cancer, stroke, a metabolic disease (e.g., obesity or diabetes), a mitochondrial disorder, depression, migraines (e.g., chronic migraines), Rett syndrome, attention deficit disorder, fragile X syndrome, or traumatic brain injury (TBI). In some embodiments, the compositions and methods provided herein are useful in treating or preventing aging or aging-associating conditions. In some embodiments, the compositions and methods provided herein can replace the ketogenic diet in the treatment or prevention of a condition described herein, in other embodiments, the compositions and methods provided herein can be combined with the ketogenic diet. More information on conditions may be found in Stafstrom et al. (2012) *Front. Pharmacol.* 3:59, hereby incorporated in its entirety.

The composition may be formulated for oral delivery. In some embodiments, the composition may comprise probiotics. In some embodiments, the compositions disclosed herein are food products. The composition may be in the form of a pill, tablet, or capsule. In some embodiments, the subject may be a mammal (e.g., a human). In some embodiments, the composition is self-administered. While it is preferred for a single composition to comprise all the bacteria to be administered, it will be recognized that for any of the various embodiments described herein, the combination of bacteria can similarly be administered in multiple compositions that together comprise the combination of bacteria. For example, the invention further provides kits comprising multiple compositions that together comprises bacteria of *Akkermansia* genus (e.g., *Akkermansia muciniphila*) and *Parabacteroides* genus (e.g., *Parabacteroides merdae* or *Parabacteroides distasonis*).

In some embodiments, the composition is formulated for rectal delivery (e.g., a fecal sample). In some embodiments, the subject undergoes fecal microbiota transplant, wherein the transplant comprises a composition disclosed herein. Fecal microbiota transplantation (FMT), also commonly known as 'fecal bacteriotherapy' represents a therapeutic protocol that allows the reconstitution of colon microbial communities. The process involves the transplantation of fecal bacteria from a healthy individual into a recipient. FMT restores colonic microflora by introducing healthy bacterial flora through infusion of a fecal sample, e.g., by enema, orogastric tube or by mouth in the form of a capsule containing freeze-dried material, obtained from a healthy donor. In some embodiments, the fecal sample is from a fecal bank.

In some embodiments, the bacterial DNA in subject's gut microbiota is sequenced. The subject's gut bacterial DNA may be sequenced prior to administration of the composition. For example, a sample comprising bacterial DNA may be obtained from the subject, and the bacterial DNA is then sequenced for *Akkermansia* (Akk) and/or *Parabacteroides* DNA, therefore measuring the presence or level of *Akkermansia* and/or *Parabacteroides* in the subject's gut microbiota. The composition disclosed herein may then be administered to the subject if the level of *Akkermansia* and/or *Parabacteroides* is low. In some embodiments, the subject is deemed to have low levels of *Akkermansia* and/or *Parabacteroides* if less than 0.0001%, less than 0.001%, less than 0.01%, less than 0.02%, less than 0.03%, less than 0.04%, less than 0.05%, less than 0.06% less than 0.07%, less than 0.08%, less than 0.09%, less than 1%, less than 0.2%, less than 0.3% less than 0.4%, less than 0.5%, less than 0.6%, less than 0.7%, less than 0.8%, less than 0.9%, less than 1%, less than 2%, less than 3%, less than 5%, less than 7%, less than 10%, less than 20%, less than 30%, less than 40%, or less than 50% of the bacteria in the sample is *Akkermansia* and/or *Parabacteroides* DNA. Bacterial DNA to be sequenced may be obtained through any means known in the art, including, but not limited to, obtaining a fecal sample from the subject and isolating the bacterial DNA. Bacterial DNA sequencing by any known technique in the art, including, but not limited to, Maxam Gilbert sequencing, Sanger sequencing, shotgun sequencing, bridge PCR, or next generation sequencing methods, such as massively parallel signature sequencing (MPSS), polony sequencing, 454 pyrosequencing, Illumina (Solexa) sequencing, SOLID sequencing, Ion torrent semiconductor sequencing, DNA nanoball sequencing, heliscope single molecule sequencing, single molecule real time (SMRT) sequencing, or nanopore DNA sequencing.

In some embodiments, the above methods directly act to reduce the amount of pathogenic bacteria in a subject (i.e., in the gastrointestinal tract of the subject). In some embodiments, this includes any such therapy that achieves the same goal of reducing the number of pathogenic organisms, when used in combination with the compositions described herein, would lead to replacement of the pathogenic microflora involved in the diseased state with natural microflora associated with a non-diseased state, or less pathogenic species occupying the same ecological niche as the type causing a disease state. For example, a subject may undergo treatment with antibiotics (e.g., antimicrobial compounds) or a composition comprising antibiotics to target and decrease the prevalence of pathogenic organisms, and subsequently be treated with a composition described herein. The treatment may also comprise an antifungal or anti-viral compound.

Suitable antimicrobial compounds include capreomycins, including capreomycin IA, capreomycin IB, capreomycin IIA and capreomycin IIB; carbomycins, including carbomycin A; carumonam; cefaclor, cefadroxil, cefamandole, cefatrizine, cefazedone, cefazolin, cefbuperazone, cefcapene pivoxil, cefclidin, cefdinir, cefditoren, cefime, ceftamet, cefmenoxime, cefmetzole, cefminox, cefodizime, cefonicid, cefoperazone, ceforanide, cefotaxime, cefotetan, cefotiam, cefoxitin, cefpimizole, cefpiramide, cefpirome, cefprozil, cefroxadine, cefsulodin, ceftazidime, cefteram, ceftezole, ceftibuten, ceftiofur, ceftizoxime, ceftriaxone, cefuroxime, cefuzonam, cephalexin, cephalogycin, cephaloridine, cephalosporin C, cephalothin, cephapirin, cephamycins, such as cephamycin C, cephradine, chlortetracycline; chlarithromycin, clindamycin, clometocillin, clomocycline, cloxacillin, cyclacillin, danofloxacin, demeclocyclin, destomycin A, dicloxacillin, dirithromycin, doxycyclinepicillin, erythromycin A, ethanbutol, fenbenicillin, flomoxef, florfenicol, floxacillin, flumequine, fortimicin A, fortimicin B, forfomycin, foraltadone, fusidic acid, gentamycin, glyconiazide, guamecycline, hetacillin, idarubicin, imipenem, isepamicin, josamycin, kanamycin, leumycins such as leumycin A1, lincomycin, lomefloxacin, loracarbef, lymecycline, meropenam, metampicillin, methacycline, methicillin, mezlocillin, micronomicin, midecamycins such as midecamycin A1, mikamycin, minocycline, mitomycins such as mitomycin C, moxalactam, mupirocin, nafcillin, netilicin, norcardians such as norcardian A, oleandomycin, oxytetracycline, panipenam, pazufloxacin, penamecillin, penicillins such as penicillin G, penicillin N and penicillin O, penillic acid, pentylpenicillin, peplomycin, phenethicillin, pipacyclin, piperacilin, pirlimycin, pivampicillin, pivcefalexin, porfiromycin, propiallin, quinacillin, ribostamycin, rifabutin, rifamide, rifampin, rifamycin SV, rifapentine, rifaximin, ritipenem, rekitamycin, rolitetracycline, rosaramicin, roxithromycin, sancycline, sisomicin, sparfloxacin, spectinomycin, streptozocin, sulbenicillin, sultamicillin, talampicillin, teicoplanin, temocillin, tetracyclin, thostrepton, tiamulin, ticarcillin, tigemonam, tilmicosin, tobramycin, tropospectromycin, trovafloxacin, tylosin, and vancomycin, and analogs, derivatives, pharmaceutically acceptable salts, esters, prodrugs, and protected forms thereof.

Suitable anti-fungal compounds include ketoconazole, miconazole, fluconazole, clotrimazole, undecylenic acid, sertaconazole, terbinafine, butenafine, clioquinol, haloprogin, nystatin, naftifine, tolnaftate, ciclopirox, amphotericin B, or tea tree oil and analogs, derivatives, pharmaceutically acceptable salts, esters, prodrugs, and protected forms thereof.

Suitable antiviral agents include acyclovir, azidouridine, anismoycin, amantadine, bromovinyldeoxusidine, chlorovinyldeoxusidine, cytarabine, delavirdine, didanosine, deoxynojirimycin, dideoxycytidine, dideoxyinosine, dideoxynucleoside, desciclovir, deoxyacyclovir, efavirenz, enviroxime, fiacitabine, foscamet, fialuridine, fluorothymidine, floxuridine, ganciclovir, hypericin, idoxuridine, interferon, interleukin, isethionate, nevirapine, pentamidine, ribavirin, rimantadine, stavudine, sargramostin, suramin, trichosanthin, tribromothymidine, trichlorothymidine, trifluorothymidine, trisodium phosphomonoformate, vidarabine, zidoviridine, zalcitabine and 3-azido-3-deoxythymidine and analogs, derivatives, pharmaceutically acceptable salts, esters, prodrugs, and protected forms thereof.

Other suitable antiviral agents include 2',3'-dideoxyadenosine (ddA), 2',3'-dideoxyguanosine (ddG), 2',3'-dideoxycytidine (ddC), 2',3'-dideoxythymidine (ddT), 2'3'-dideoxy-dideoxythymidine (d4T), 2'-deoxy-3'-thia-cytosine (3TC or lamivudine), 2',3'-dideoxy-2'-fluoroadenosine, 2',3'-dideoxy-2'-fluoroinosine, 2',3'-dideoxy-2'-fluorothymidine, 2',3'-dideoxy-2'-fluorocytosine, 2'3'-dideoxy-2',3'-didehydro-2'-fluorothymidine (Fd4T), 2'3'-dideoxy-2'-beta-fluoroadenosine (F-ddA), 2'3'-dideoxy-2'-beta-fluoroinosine (F-ddI), and 2',3'-dideoxy-2'-beta-flurocytosine (F-ddC). In some embodiments, the antiviral agent is selected from trisodium phosphomonoformate, ganciclovir, trifluorothymidine, acyclovir, 3'-azido-3'-thymidine (AZT), dideoxyinosine (ddI), and idoxuridine and analogs, derivatives, pharmaceutically acceptable salts, esters, prodrugs, and protected forms thereof.

Compositions

In some aspects, the invention relates to a composition (e.g., a food product or a pharmaceutical composition) comprising bacteria of *Akkermansia* (Akk) and *Parabacteroides* (Pb) genera. The composition may comprise a pharmaceutically acceptable carrier. The composition may comprise probiotics. The pharmaceutical compositions disclosed herein may be delivered by any suitable route of administration, including orally, bucally, sublingually, parenterally, and rectally, as by powders, ointments, drops, liquids, gels, tablets, capsules, pills, or creams. In certain embodiments, the pharmaceutical compositions are delivered generally (e.g., via oral administration). In certain other embodiments, the compositions disclosed herein are delivered rectally.

In certain embodiments, the invention provides kits comprising multiple compositions that together comprises bacteria of *Akkermansia* genus (e.g., *Akkermansia muciniphila*) and *Parabacteroides* genus (e.g., *Parabacteroides merdae* or *Parabacteroides distasonis*) (e.g., that, if combined, would result in a composition as described anywhere in this section).

The composition may comprise any species of *Parabacteroides*, including, but not limited to, *P. chartae, P. chinchillae, P. distasonis, P. faecis, P. goldsteinii, P. gordonii, P. johnsonii*, or *P. merdae*. In some embodiments, at least 1%, at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, or at least 95%, of the bacteria in the composition are *Parabacteroides* (Pb) bacteria. The bacteria of *Akkermansia* in the composition may comprise *Akkermansia muciniphila*. In some embodiments, the compositions disclosed herein may comprise at least 1%, at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, or at least 95% *Akkermansia* bacteria.

Compositions described herein may be used for oral administration to the gastrointestinal tract, directed at the objective of introducing the bacteria (e.g., the bacteria disclosed herein) to tissues of the gastrointestinal tract. The formulation for a composition (e.g., a probiotic composition) of the present invention may also include other probiotic agents or nutrients which promote spore germination and/or bacterial growth. An exemplary material is a bifidogenic oligosaccharide, which promotes the growth of beneficial probiotic bacteria. In some embodiments, the probiotic bacterial composition is administered with a therapeutically-effective dose of an (preferably, broad spectrum) antibiotic, or an anti-fungal agent. In some embodiments, the compositions described herein are encapsulated into an enterically-coated, time-released capsule or tablet. The enteric coating allows the capsule/tablet to remain intact (i.e., undissolved) as it passes through the gastrointestinal tract, until after a certain time and/or until it reaches a certain part of the GI tract (e.g., the small intestine). The time-released component prevents the "release" of the probiotic bacterial strain in the compositions described herein for a pre-determined time period.

The composition may be a food product, such as, but not limited to, a dairy product. The dairy product may be cultured or a non-cultured (e.g., milk) dairy product. Non-limiting examples of cultured dairy products include yogurt, cottage cheese, sour cream, kefir, buttermilk, etc. Dairy products also often contain various specialty dairy ingredients, e.g. whey, non-fat dry milk, whey protein concentrate solids, etc. The dairy product may be processed in any way known in the art to achieve desirable qualities such as flavor, thickening power, nutrition, specific microorganisms and other properties such as mold growth control. The compositions of the present invention may also include known antioxidants, buffering agents, and other agents such as coloring agents, flavorings, vitamins, or minerals.

In some embodiments, the compositions of the present invention are combined with a carrier (e.g., a pharmaceutically acceptable carrier) which is physiologically compatible with the gastrointestinal tissue of the subject(s) to which it is administered. Carriers can be comprised of solid-based, dry materials for formulation into tablet, capsule or powdered form; or the carrier can be comprised of liquid or gel-based materials for formulations into liquid or gel forms. The specific type of carrier, as well as the final formulation depends, in part, upon the selected route(s) of administration. The therapeutic composition of the present invention may also include a variety of carriers and/or binders. In some embodiments, the carrier is micro-crystalline cellulose (MCC) added in an amount sufficient to complete the one gram dosage total weight. Carriers can be solid-based dry materials for formulations in tablet, capsule or powdered form, and can be liquid or gel-based materials for formulations in liquid or gel forms, which forms depend, in part, upon the routes of administration. Typical carriers for dry formulations include, but are not limited to: trehalose, malto-dextrin, rice flour, microcrystalline cellulose (MCC) magnesium sterate, inositol, FOS, GOS, dextrose, sucrose, and like carriers. Suitable liquid or gel-based carriers include but are not limited to: water and physiological salt solutions; urea; alcohols and derivatives (e.g., methanol, ethanol, propanol, butanol); glycols (e.g., ethylene glycol, propylene glycol, and the like). Preferably, water-based carriers possess a neutral pH value (i.e., pH 7.0). Other carriers or agents for administering the compositions described herein are known in the art, e.g., in U.S. Pat. No. 6,461,607.

In some embodiments, the composition further comprises other bacteria or microorganisms known to colonize the gastrointestinal tract. For example, the composition may comprise species belonging to the Firmicutes phylum, the Proteobacteria phylum, the Tenericutes phylum, the Actinobacteria phylum, or a combination thereof. Examples of additional bacteria and microorganisms that may be included in the subject compositions include, but are not limited to, *Saccharomyces*, *Bacteroides*, *Eubacterium*, *Clostridium*, *Lactobacillus*, *Fusobacterium*, *Propionibacterium*, *Streptococcus*, *Enteroccus*, *Lactococcus* and *Staphylococcus*, *Peptostreptococcus*. In certain embodiments, the composition is substantially free of bacteria that increase the risk of seizures or otherwise detract from the effect of a ketogenic diet Such bacteria include *Bifidobacterium* bacteria. Thus, in some embodiments, the composition is substantially free of *Bacteroides* bacteria. A composition is substantially free of a bacterial type if that type makes up less than 10% of the bacteria in a composition, preferably less than 5%, even more preferably less than 1%, most preferably less than 0.5%, or even 0% of the bacteria in the composition.

In some embodiments, the composition comprises a fecal sample comprising at least one species of *Akkermansia* (Akk) and at least one species of *Parabacteroides* (Pb). In some embodiments, the fecal sample is from a fecal bank. In some embodiments, the compositions may be added to a fecal sample prior to administration to the subject.

In some embodiments, provided herein are methods of treating or preventing a condition, such as seizures, by administering a composition (e.g., a fecal sample) that is enriched for at least one species of *Akkermansia* (Akk) and at least one species of *Parabacteroides* (Pb) to the subject. The fecal sample is enriched if at least 0.01%, at least 0.02%, at least 0.03%, at least 0.04%, at least 05%, at least 0.06%, at least 0.07%, at least 0.08%, at least 09%, at least 0.1%, at least 0.2%, at least 0.3%, at least 0.4%, at least 0.5%, at least 0.6%, at least 0.7%, at least 0.8%, at least 0.9%, at least 1%, or at least 2%, at least 3%, at least 4%, at least 5%, at least 6%, at least 7%, at least 8%, at least 9%, at least 10%, at least 15%, at least 20%, at least 25%, at least 30%, at least 35%, at least 40%, at least 45%, or at least 50% of the bacteria in the fecal sample is *Akkermansia* (Akk). In some embodiments, fecal sample is enriched if at least 0.01%, at least 0.02%, at least 0.03%, at least 0.04%, at least 0.05%, at least 0.06%, at least 0.07%, at least 0.08%, at least 0.09%, at least 0.1%, at least 0.2%, at least 0.3%, at least 0.4%, at least 0.5%, at least 0.6%, at least 0.7%, at least 0.8%, at least 0.9%, at least 1%, or at least 2%, at least 3%, at least 4%, at least 5%, at least 6%, at least 7%, at least 8%, at least 9%, at least 10%, at least 15%, at least 20%, at least 25%, at least 30%, at least 35%, at least 40%, at least 45%, or at least 50% of the bacteria in the fecal sample is and *Parabacteroides* (Pb). In some embodiments, the fecal sample is from a fecal bank. In some embodiments, the fecal sample is from a donor.

The composition may further comprise a nutrient. In some embodiments, the nutrient aids in the growth of bacteria (e.g., bacteria disclosed herein). In some embodiments, the nutrient is a component listed in FIG. 12. In some embodiments, the nutrient is a lipid (e.g., lineoleic acid, stearic acid, or palmitic acid). In some embodiments, the nutrient may be conjointly administered with a composition disclosed herein. As used herein, the phrase "conjoint administration" refers to any form of administration of two or more different agents (e.g., a composition disclosed herein and a nutrient disclosed herein) such that the second agent is administered while the previously administered agent is still effective in the body. For example, the compositions disclosed herein and the nutrients disclosed herein can be administered either in the same formulation or in a separate formulation, either concomitantly or sequentially.

Actual dosage levels of the active ingredients in the pharmaceutical compositions may be varied so as to obtain an amount of the active ingredient which is effective to achieve the desired therapeutic response for a particular patient, composition, and mode of administration, without being toxic to the patient.

The selected dosage level will depend upon a variety of factors including the activity of the particular agent employed, the route of administration, the time of administration, the rate of excretion or metabolism of the particular compound being employed, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could prescribe and/or administer doses of the compounds employed in the pharmaceutical composition at levels lower than that required in order to achieve the desired therapeutic effect and gradually increase the dosage until the desired effect is achieved.

The invention now being generally described, it will be more readily understood by reference to the following examples, which are included merely for purposes of illustration of certain aspects and embodiments of the present invention, and are not intended to limit the invention.

EXEMPLIFICATION

Example 1: Materials and Methods

Animals and Diets

Three to four week old SPF wild type Swiss Webster mice (Taconic Farms), GF wild type Swiss Webster mice (Taconic Farms) and SPF C3HeB/FeJ KCNA1 KO mice (Jackson Laboratories) were bred in UCLA's Center for Health Sciences Barrier Facility. Breeding animals were fed "breeder" chow (Lab Diets 5K52). Experimental animals were fed standard chow (Lab Diet 5010), 6:1 ketogenic diet (Harlan Teklad TD.07797.PWD) or vitamin- and mineral-matched control diet (Harlan Teklad TD.150300). Juvenile mice were used to i) mimic the typical use of the KD to treat pediatric and adolescent epileptic patients, ii) align the timing of mouse brain development to early human brain development, where neurodevelopmental milestones in 3-week old mice are comparable to those of the 2-3 year old human brain[60], and iii) preclude pre-weaning dietary treatment, where effects of the diet on maternal behavior and physiology would confound direct effects of the diet on offspring. Mice were randomly assigned to an experimental group. All animal experiments were approved by the UCLA Animal Care and Use Committee.

6-Hz Psychomotor Seizure Assay

The 6-Hz test was conducted as previously described[13]. Pilot studies revealed no sexual dimorphism in seizure threshold. All subsequent experimental cohorts contained male mice. One drop (~50 ul) of 0.5% tetracaine hydrochloride ophthalmic solution was applied to the corneas of each mouse 10-15 min before stimulation. Corneal electrodes were coated with a thin layer of electrode gel (Parker Signagel). A constant-current current device (ECT Unit 57800, Ugo Basile) was used to deliver current at 3 sec duration, 0.2 ms pulse-width and 6 pulses/s frequency. CC50 (the intensity of current required to elicit seizures in 50% of the experimental group) was measured as a metric for seizure susceptibility. Pilot experiments were conducted to identify 24 mA as the CC50 for SPF wild-type Swiss Webster mice. Each mouse was seizure-tested only once, and thus at least n>6 mice were used to adequately power each experiment group. To determine CC50s for each experimental group, 24 mA currents were administered to the first mouse per experimental group per cohort, followed by fixed increases or decreases by 2 mA intervals. Mice were restrained manually during stimulation and then released into a new cage for behavioral observation. Locomotor behavior was recorded using Ethovision XT software (Noldus) and quantitative measures for falling, tail dorsiflexion (Straub tail), forelimb clonus, eye/vibrissae twitching and behavioral remission were scored manually. For each behavioral parameter, we observed no correlation between percentage incidence during 24 mA seizures and microbiota status or group seizure susceptibility, suggesting a primary effect of the microbiota on seizure incidence rather than presentation or form. Latency to exploration (time elapsed from when an experimental mouse is released into the observation cage (after corneal stimulation) to its first lateral movement) was scored using Ethovision and manually with an electronic timer Within-diet groups were tested blindly. Authentic blinding across different-diet groups was not possible due to diet-induced changes in stool color. However, results from pilot experiments reveal no significant differences between results acquired from the same experimental groups tested blinded vs non-blinded. Mice were scored as protected from seizures if they did not show seizure behavior and resumed normal exploratory behavior within 10 s. Seizure threshold (CC50) was determined as previously described[61], using the average log interval of current steps per experimental group, where sample n is defined as the subset of animals displaying the less frequent seizure behavior. Data used to calculate CC50 are also displayed as latency to explore for each current intensity, where n represents the total number of biological replicates per group regardless of seizure outcome.

Glucose Measurements

Blood samples were collected by cardiac puncture and spun through SST vacutainers (Becton Dickinson) for serum separation. Glucose levels were detected in sera by colorimetric assay according to the manufacturer's instructions (Cayman Chemical). Data compiled across multiple experiments are expressed as glucose concentrations normalized to SPF controls within each experiment.

Beta-Hydroxybutyrate (BHB) Measurements

Blood was collected by cardiac puncture and spun through SST vacutainers (Becton Dickinson) for serum separation. The colon was washed and flushed with PBS to remove lumenal contents. Frontal cortex, hippocampus, hypothalamus and cerebellum were microdissected and livers were harvested and washed in PBS. Tissue samples were sonicated on ice in 10 s intervals at 20 mV in RIPA lysis buffer (Thermo Scientific). BHB levels were detected in sera by colorimetric assay according to the manufacturer's instructions (Cayman Chemical). Data were normalized to total protein content as detected by BCA assay (Thermo Pierce). Data compiled across multiple experiments are expressed as BHB concentrations normalized to SPF controls within each experiment.

16S rDNA Microbiome Profiling

Bacterial genomic DNA was extracted from mouse fecal samples or colonic lumenal contents using the MoBio PowerSoil Kit, where the sample n reflects independent cages containing 3 mice per cage. The library was generated according to methods adapted from 62. The V4 regions of the 16S rDNA gene were PCR amplified using individually barcoded universal primers and 30 ng of the extracted genomic DNA. The PCR reaction was set up in triplicate, and the PCR product was purified using the Qiaquick PCR purification kit (Qiagen). The purified PCR product was pooled in equal molar concentrations quantified by the Kapa library quantification kit (Kapa Biosystems, KK4824) and sequenced by Laragen, Inc. using the Illumina MiSeq platform and 2×250 bp reagent kit for paired-end sequencing Operational taxonomic units (OTUs) were chosen by open reference OTU picking based on 97% sequence similarity to the Greengenes 13_5 database. Taxonomy assignment and rarefaction were performed using QIIME1.8.0[63] using 85,134 reads per sample. Metagenomes were inferred from closed reference OTU tables using PICRUSt[64]. Results were filtered to display the top 72 genes relevant to amino acid metabolism in FIG. S7C.

Microbiota Conventionalization

Fecal samples were freshly collected from adult SPF Swiss Webster mice and homogenized in pre-reduced PBS at 1 ml per pellet. 100 ul of the settled suspension was administered by oral gavage to recipient GF mice. For mock treatment, mice were gavaged with pre-reduced PBS.

Antibiotic Treatment

SPF mice were gavaged with a solution of vancomycin (50 mg/kg), neomycin (100 mg/kg) and metronidazole (100 mg/kg) every 12 hours daily for 7 days, according to methods previously described by Reikvam et al., PloS one (6), 2011. Ampicillin (1 mg/ml) was provided ad libitum in drinking water. For mock treatment, mice were gavaged with normal drinking water every 12 hours daily for 7 days. For Kcna1$^{-/-}$ mice, drinking water was supplemented with vancomycin (500 mg/ml), neomycin (1 mg/ml) and ampicillin (1 mg/ml) for 1 week to preclude the stress of oral gavage in seizure-prone mice.

Gnotobiotic Colonization and Bacterial Enrichment in Antibiotic-Treated Mice

*A. muciniphila* (ATCC BAA845) was cultured under anaerobic conditions in Brain Heart Infusion (BHI) media supplemented with 0.05% hog gastric mucin type III (Sigma Aldrich). *P. merdae* (ATCC 43184) and *P. distasonis* (ATCC 8503) were grown in anaerobic conditions in Reinforced Clostridial Media (RCM). $10^9$ cfu bacteria were suspended in 200 ul pre-reduced PBS and orally gavaged into antibiotic-treated mice or germ-free mice. When co-administered as "*A. muciniphila* and *Parabacteroides* spp.", a ratio of 2:1:1 was used for *A. muciniphila: P. merdae: P. distasonis*. For mock treatment, mice were gavaged with pre-reduced PBS. Pilot studies revealed no significant differences between colonization groups in fecal DNA concentration or 16S rDNA amplification, as measures relevant to bacterial load. Mice were maintained in microisolator cages and handled aseptically. Mice were seizure tested at 14 days after colonization.

Fecal Microbiota Transplant

Fecal samples were freshly collected from donor mice fed KD or CD for 14 days and suspended at 50 mg/ml in pre-reduced PBS. Antibiotic-treated mice were colonized by oral gavage of 100 ul suspension. For mock treatment, mice were gavaged with pre-reduced PBS. Mice were housed in microisolator cages and handled aseptically. Seizure testing was conducted at 4 days after transplant.

Bacterial Treatment

*A. muciniphila, P. merdae* and *P. distasonis* were freshly cultured in anaerobic conditions as described above, and then washed, pelleted and re-suspended at $5 \times 10^9$ cfu/ml in pre-reduced PBS. *A. muciniphila* with *Parabacteroides* spp. were prepared at a 2:1:1 ratio. For heat-killing, bacteria were placed at 95° C. for 10 min. Mice were gavaged every 12 hours for 28 days with 200 ul bacterial suspension or sterile pre-reduced PBS as vehicle control.

Kcna1 Seizure Recordings

EEG Implantation and Recovery.

EEGs were recorded from male and female Kcna1$^{-/-}$ mice at 6-7 weeks of age. Kcna1$^{+/+}$ littermates were used as controls. We observed no significant differences between males and females in seizure frequency and duration. Data presented include both sexes. Mice were anesthetized with isoflurane (5% induction, 2% maintenance) and eye ointment applied to each eye. Fur was removed along the head, and the area was cleaned with three alternative scrubs of chlorhexidine and 70% isopropanol. In a biosafety cabinet, mice were positioned in a stereotaxic apparatus (Harvard Biosciences) and 1 mg/kg lidocaine+1 mg/kg bupivacaine was applied locally along the incision site. Using sterile surgical tools, a 2 cm incision was made along the dorsal midline from the posterior margin of the eyes to a point midway between the scapulae. A subcutaneous pocket along the dorsal flank was created and the pocket irrigated with sterile saline. A wireless telemetry transmitter was inserted with bi-potential leads oriented cranially. The skull was cleaned with 3% hydrogen peroxide followed by 70% isopropanol. Using a 1.0 mm micro drill bit, the skull was perforated to generate two small holes halfway between the bregma and lambda, and 1-2 mm from the sagittal suture. Bilateral EEG recording electrodes (Data Sciences International (DSI) PhysioTel, ETA-F10) were epidurally implanted over the frontoparietal cortex. Sterile acrylic was applied to the dried area. The incision site was closed with absorbable 5-0 sutures and cleaned with 3% hydrogen peroxide followed by 70% ethanol. Animals were housed individually in autoclaved microisolator cages and allowed to recover for 3-5 days before recordings were initiated Data Acquisition and Analysis During EEG recordings animals were freely moving and maintained on experimental diet. EEG traces were acquired over 3 days using the DSI Ponemah V5.1 data acquisition system. Simultaneous video recordings of behavioral seizures were correlated with EEG recordings and scored based on an adapted Racine scale and defined by 5 stages: 1) myoclonic jerk, 2) head stereotypy and facial clonus, 3) bilateral and alternating forelimb/hindlimb clonus, 4) rearing and falling, and 5) generalized tonic-clonic episodes. Data were analyzed by a blinded researcher using Neuroscore CNS Software (DSI). EEG signals were filtered using a 10 Hz high pass filter, and seizure events were detected by blinded manual scoring. Seizures were defined as patterns of high-frequency, high-voltage synchronized heterogeneous spike wave forms with amplitudes at least 2-fold greater than background with more than 6 s duration. The spike frequency was determined as number of spikes occurring above baseline in a given seizure, and the interspike interval was analyzed as a function of the time between spikes for five representative seizures in each phase per mouse. The duration of maximum spike amplitude was determined as the percent time spent in spikes that were three times as large as the baseline for five representative seizures in each phase per mouse.

Colonic Lumenal and Serum Metabolomics

Samples were collected from mice housed across independent cages, with at least 2 mice per cage. Colonic lumenal contents were collected from terminal mouse dissections, immediately snap frozen in liquid nitrogen and stored at −80° ° C. Serum samples were collected by cardiac puncture, separated using SST vacutainer tubes and frozen at −80° ° C. Samples were prepared using the automated MicroLab STAR system (Hamilton Company) and analyzed on GC/MS, LC/MS and LC/MS/MS platforms by Metabolon, Inc. Protein fractions were removed by serial extractions with organic aqueous solvents, concentrated using a Turbo Vap system (Zymark) and vacuum dried. For LC/MS and LC-MS/MS, samples were reconstituted in acidic or basic LC-compatible solvents containing >11 injection standards and run on a Waters ACQUITY UPLC and Thermo-Finnigan LTQ mass spectrometer, with a linear ion-trap front-end and a Fourier transform ion cyclotron resonance mass spectrometer back-end. For GC/MS, samples were derivatized under dried nitrogen using bistrimethyl-silyl-trifluoroacetamide and analyzed on a Thermo-Finnigan Trace DSQ fast-scanning single-quadrupole mass spectrometer using electron impact ionization. Chemical entities were identified by comparison to metabolomic library entries of purified standards. Following log transformation and imputation with minimum observed values for each compound, data were analyzed using one-way ANOVA to test for group effects. P and q-values were calculated based on two-way ANOVA contrasts. Principal components analysis was used to visualize variance distributions. Supervised Random Forest analysis was conducted to identify metabolomics prediction accuracies.

Hippocampal Metabolomics

Hippocampal tissues were homogenized in 1 ml cold 80% MeOH and vigorously mixed on ice followed by centrifugation ($1.3*10^4$ rpm, 4° C.). 5 ug supernatant was transferred into a glass vial, supplemented with 5 nmol D/L-norvaline, dried down under vacuum, and finally re-suspended in 70% acetonitrile. For the mass spectrometry-based analysis of the sample, 5 l were injected onto a Luna NH2 (150 mm×2 mm, Phenomenex) column. The samples were analyzed with an UltiMate 3000RSLC (Thermo Scientific) coupled to a Q Exactive mass spectrometer (Thermo Scientific). The Q Exactive was run with polarity switching (+4.00 kV/−4.00 kV) in full scan mode with an m/z range of 70-1050. Separation was achieved using A) 5 mM $NH_4AcO$ (pH 9.9) and B) ACN. The gradient started with 15% A) going to 90% A) over 18 min, followed by an isocratic step for 9 min. and reversal to the initial 15% A) for 7 min. Metabolites were quantified with TraceFinder 3.3 using accurate mass measurements (≤3 ppm), retention times of pure standards and MS2 fragmentation patterns. Data analysis, including principal component analysis and hierarchical clustering was performed using R.

Amino Acid Supplementation

Four-week old Swiss Webster SPF mice were treated with antibiotics, colonized with *A. muciniphila* and *Parabacteroides* spp., and fed KD for 14 days, as described in methods above. Beginning on the evening of day 11, mice were injected intraperitoneally every 12 hours for 3 days with ketogenic amino acid cocktail (Sigma Aldrich)—L-leucine (2.0 mg/kg), L-lysine (2.0 mg/kg), L-tyrosine (2.4 mg/kg), L-tryptophan (1.6 mg/kg), and L-threonine (3.1 mg/kg) in sterile PBS. Concentrations are based on physiological levels reported for each amino acid in mouse blood[26] and on fold-changes observed in our metabolomics dataset for each amino acid between control SPF CD and AkkPb KD mice (Table S4). Vehicle-treated mice were injected with PBS (200 ul/30 g mouse). On day 14, mice were tested for 6-Hz seizures 2 hours after the final morning amino acid injection, with a prior 1-hour acclimation period in the behavioral testing room.

GGsTop Treatment

For wild type mice: 4-week old SPF Swiss Webster mice were fed CD ad libitum for 14 days. Beginning on the evening of day 11, mice were orally gavaged every 12 hours with 13.3 mg/kg 3-[[(3-amino-3-carboxypropyl)methoxyphosphinyl]oxy]benzeneacetic acid (GGsTop, Tocris Bioscience) in sterile water Vehicle-treated mice were gavaged with sterile water (200 ul/30 g mouse). On day 14, mice were tested for 6-Hz seizures 2 hours after the final morning GGsTop gavage, with a prior 1-hour acclimation period in the behavioral testing room. For Kcna1 mice: 3-4 week old $Kcna1^{-/-}$ mice were fed the CD ad libitum for 23 days. On Day 15, EEG transmitters were implanted as described in the Kcna1 Seizure Recordings section above. On the evening of day 18, mice were orally gavaged every 12 hours with 13.3 mg/kg GGsTop through the morning of day 21. Seizures were recorded over 3 days by EEG beginning 2 hours after the final gavage.

Cross-Feeding In Vitro Assay

Cross-feeding was measured as previously described. *A. muciniphila* was embedded at $2\times10^6$ cfu/ml in 5 ml pre-reduced CD or KD-based liquid media supplemented with 1% agar at the bottom of an anaerobic tube, and *P. merdae* was overlaid above it at $6\times10^6$ cfu/ml in 5 ml pre-reduced M9 minimal media. Diet-based media were generated by aseptically suspending mouse KD vs. CD diets, described above, to 2 kcal/ml in M9 media. Pilot experiments confirmed no ectopic translocation of embedded *A. miciniphila* from the agar compartment into the above M9 liquid compartment. For each time point, aliquots were taken from the top and bottom compartments, plated in a dilution series in rich media (RCM for *P. merdae* and BHI+0.05% mucins for *A. muciniphila*), and colonies were counted. For GGsTop pre-treatment experiments, *P. merdae* was incubated with 500 uM GGsTop vs vehicle in RCM media at 37° C. for 2 hours and then washed with sterile media. Pilot experiments revealed no significant effect of GGsTop pre-treatment on *P. merdae* viability.

GGT Activity Assay

GGT activity was measured as previously described in van der Stel, Frontiers in Microbiology (6), 567 (2015). For anaerobic cultures, bacteria were seeded at $3\times10^5$ cfu/ml in CD- and KD-based media. 1 ml bacterial suspension was pelleted and frozen at −80° C. for 1 hr. Separate aliquots of the same suspension were plated in BHI mucin agar media or RCM and incubated at 37° C. in a Coy anaerobic chamber for later data normalization by bacterial cfu. Pellets were then resuspended in 250 ul lysis buffer (50 mM Tris-HCl with 1 ug/ml lysozyme) and incubated on ice for 30 min. For fecal samples, one pellet was weighed and homogenized in 1 ml lysis buffer. Bacterial and fecal suspensions were then sonicated (QSonica 125) and centrifuged at 12000×g for 10 min at 4° C. 20 ul supernatant was mixed with 180 ul substrate buffer (2.9 mM L-gamma-glutamyl-3-carboxy-4-nitroanilide (Gold Bio), 100 mM of glycylglycine (Sigma Aldrich), 100 mM Tris-HCl), and 500 uM GGsTop (if noted). Absorbance at 405 nm denoting production of 3-carboxy-4-nitroaniline was measured every minute for 1 hr at 37° C using an automated multimode plate reader (Biotek Synergy H1).

Intestinal Permeability Assay

Mice were fasted for 4 hr beginning at 7 am before gavage with 0.6 g/kg 4 kDa FITC-dextran (Sigma Aldrich). 4 hours after gavage, serum samples were collected by cardiac puncture, diluted 3-fold in water and read in duplicate for fluorescence intensity at 521 nm using a Synergy H9 multimode plate reader (Biotek) against a standard dilution series of stock FITC-dextran in 3-fold diluted normal mouse serum in water.

Statistical Analysis

Statistical analysis was performed using Prism software (GraphPad). Data were assessed for normal distribution and plotted in the figures as mean±s.e.m. For each figure, n=the number of independent biological replicates. No samples or animals were excluded from the analyses. Differences between two treatment groups were assessed using two-tailed, unpaired Student/test with Welch's correction. Differences among >2 groups with only one variable were assessed using one-way ANOVA with Bonferroni post hoc test. Data for Kcna1 mice were analyzed by non-parametric one-way ANOVA with Dunn's post hoc test. Two-way ANOVA with Bonferroni post-hoc test was used for >2 groups with two variables (e.g. seizure time course, BHB time course, metabolomics data, bacterial growth curves). One-way ANOVA with repeated measures and Bonferroni post-hoc test was used for GGT assays. Significant differences emerging from the above tests are indicated in the figures by *$P<0.05$. $P<0.01$, *$P<0.001$, ****$P<0.0001$ Notable near-significant differences ($0.5<P<0.1$) are indicated in the figures. Notable non-significant (and non-near significant) differences are indicated in the figures by "n s.".

Figure 1A:
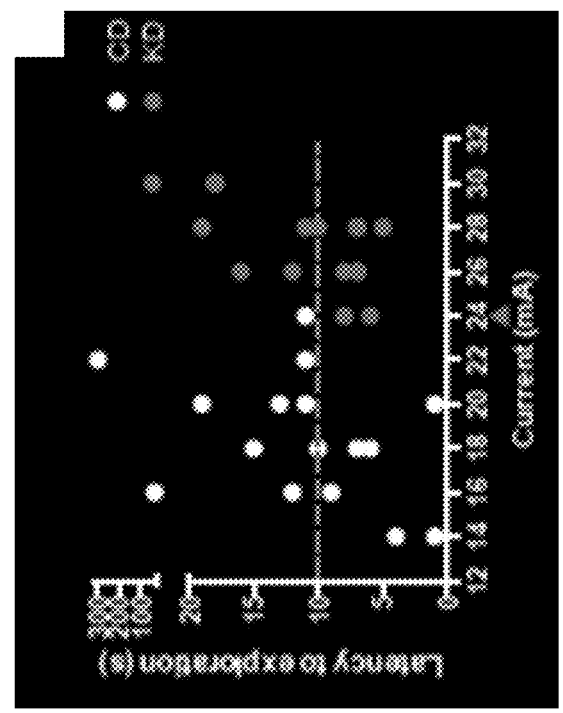
FIGS. 1A-F show seizure protection and ketogenesis in response to the ketogenic diet correlates with alterations in the gut microbiota.
Figure 1A:
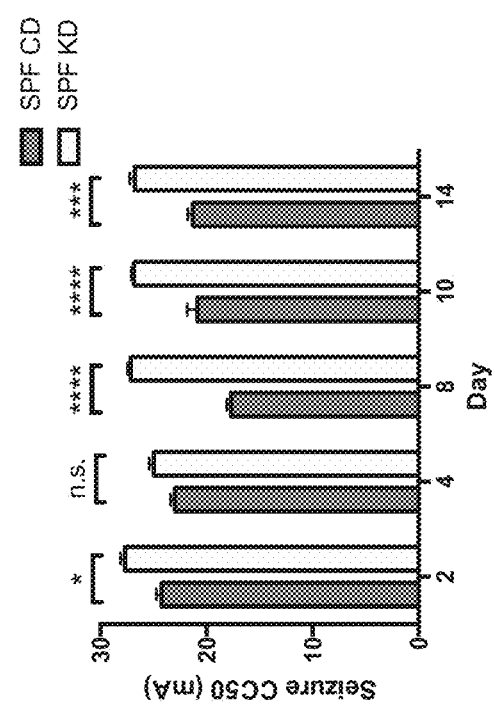
Figure 1B:
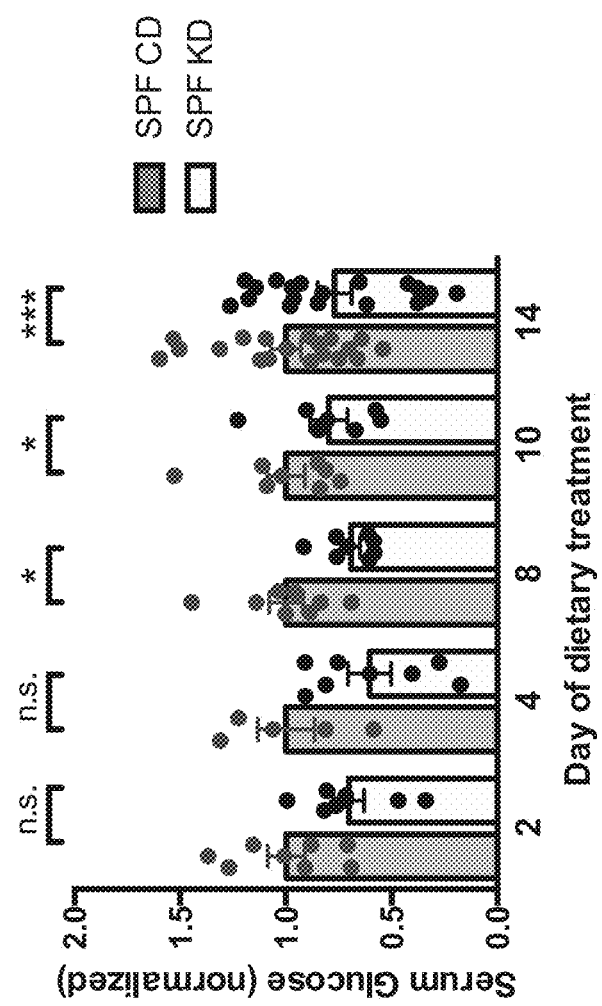
Figure 1C:
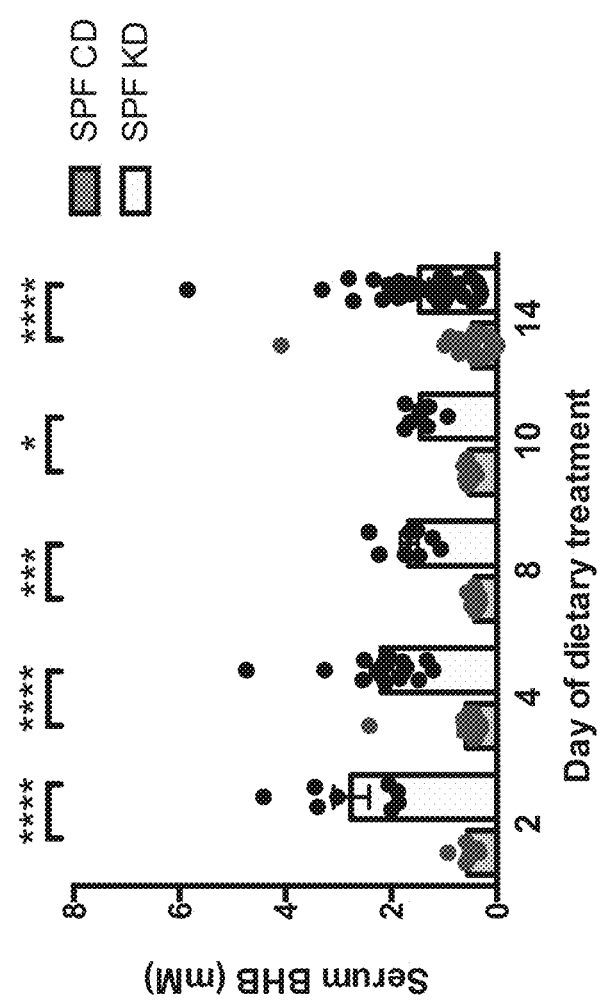

Example 2: Ketogenic Diet Alters Gut Microbiota and Confers Protection Against Seizures The 6-Hz psychomotor seizure model of refractory epilepsy involves low-frequency corneal stimulation to induce focal dyscognitive seizures reminiscent of human temporal lobe epilepsy. The KD protects against 6-Hz seizures, as indicated by the increased current intensity required to elicit a seizure in 50% of the subjects tested (CC50, seizure threshold). Specific pathogen-free (SPF) Swiss Webster mice were fed a 6:1 fat:protein KD or a vitamin- and mineral-matched control diet (CD). Compared to CD controls, mice consuming KD exhibited elevated seizure thresholds in response to 6-Hz stimulation (FIG. 1A), decreased serum glucose (FIG. 1B) and increased serum β-hydroxybutyrate (BHB; FIG. 1C). There were no significant differences in food consumption or weight gain across CD vs. KD groups.

Figure 1D:
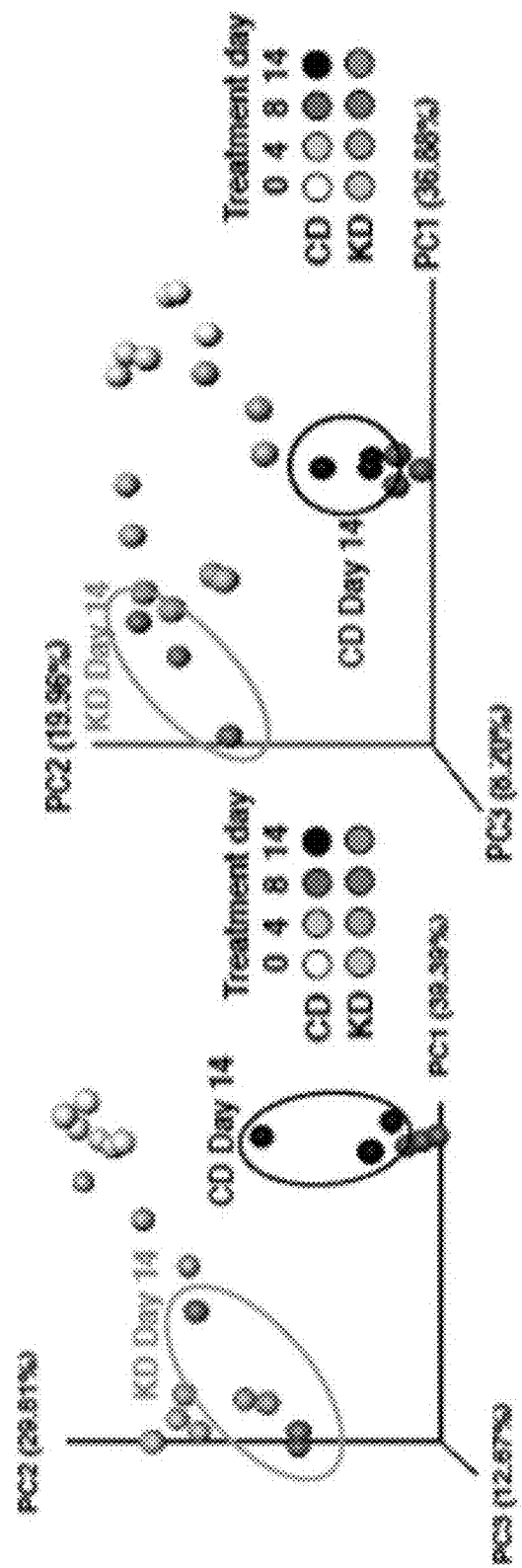
Figure 1E:
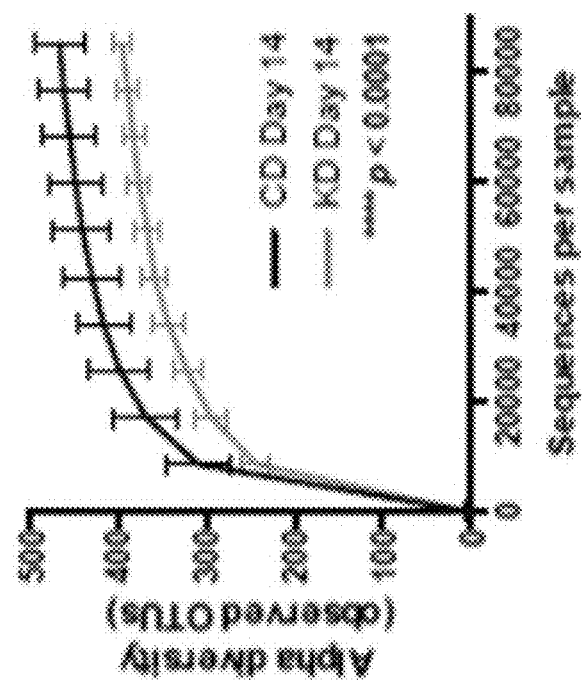
Figure 1F:
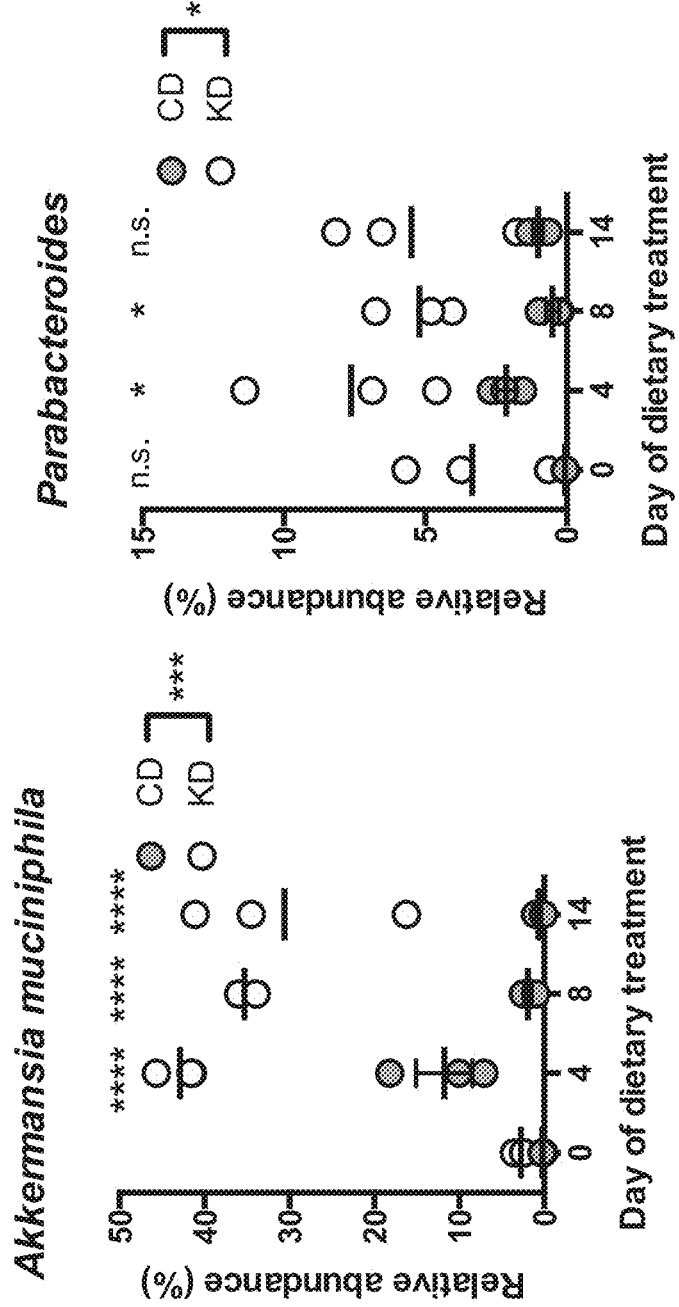
Figure 2A:
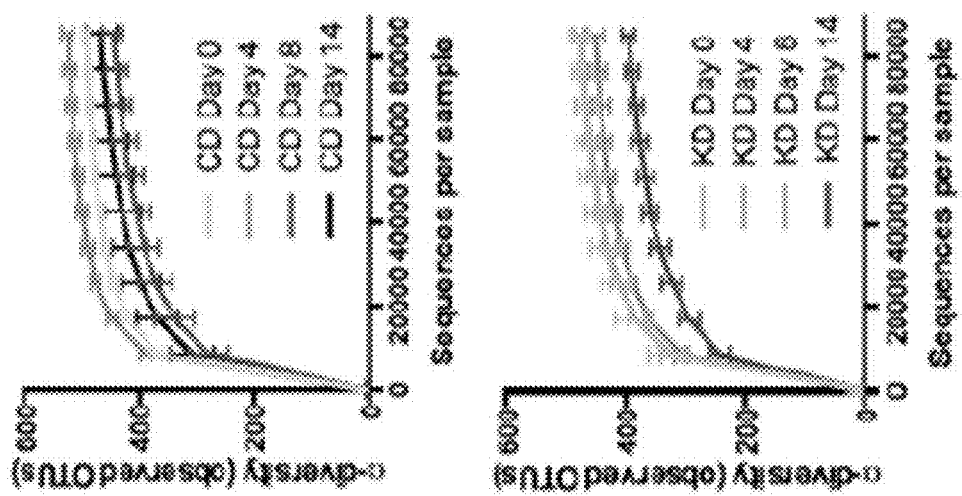
FIGS. 2A-B show the ketogenic diet enriches select bacterial species that differentiate the KD vs. CD gut microbiota.
Figure 2B:
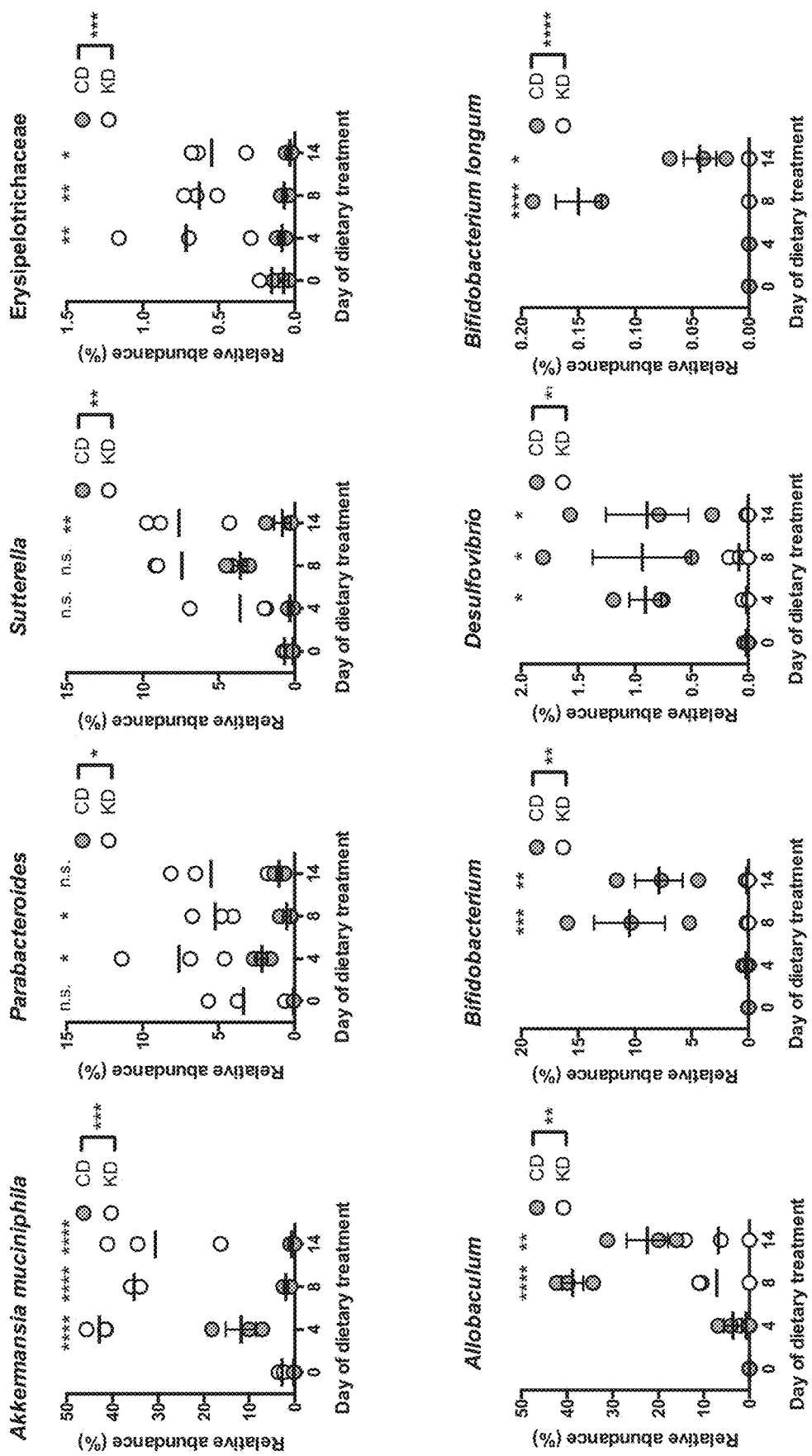

In addition to raising seizure thresholds, the ketogenic diet altered the composition of the gut microbiota (FIG. 1D), decreased α-diversity (FIG. 1E) and increased relative abundance of *Akkermansia muciniphila* (FIG. 1F). *Parabacteroides*, Sutterella and Erysipelotrichaceae spp. were also elevated in KD-fed mice, whereas *Allobaculum, Bifidobacterium* and *Desulfovibrio* spp. were elevated in mice fed the control diet (FIG. 2). These results revealed that the composition of the gut microbiota was rapidly and significantly altered in response to the KD.

Example 3: Gut Microbiota Confer the Anti-Seizure Effects of the Ketogenic Diet The 6-Hz psychomotor seizure threshold for germ-free (GF) and antibiotic (Abx)-treated SPF mice was measured in order to determine if the gut microbiota was necessary for the anti-seizure effects of the ketogenic diet.

Figure 3A:
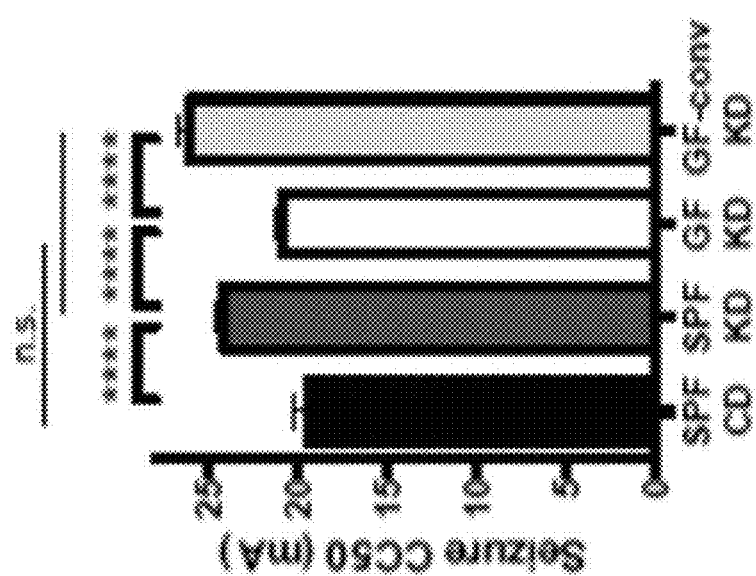
FIGS. 3A-D show the relationship of gut microbiota to the anti-seizure effects of the ketogenic diet
Figure 3B:
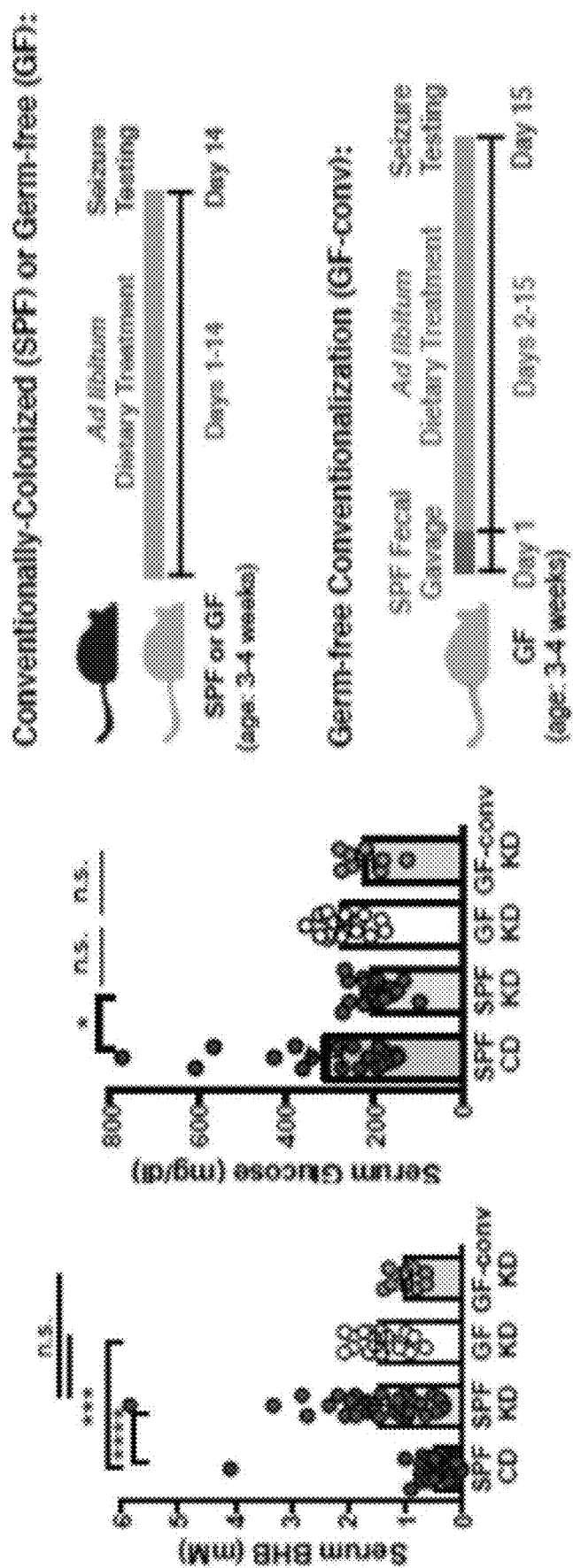
Figure 3C:
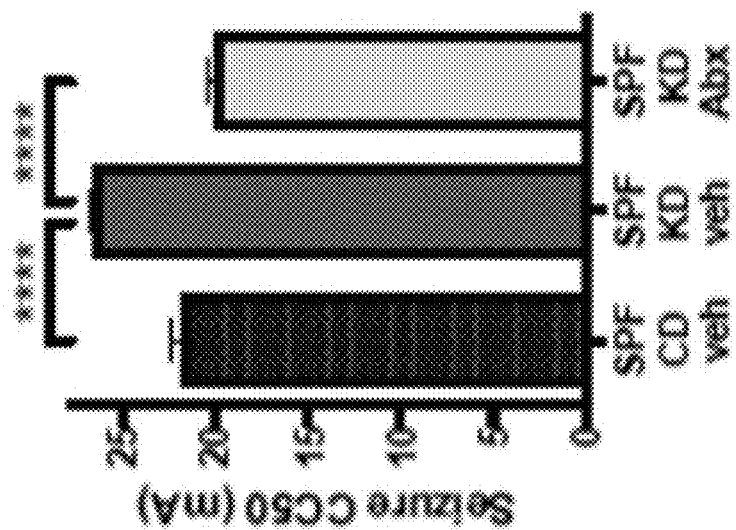
Figure 3D:
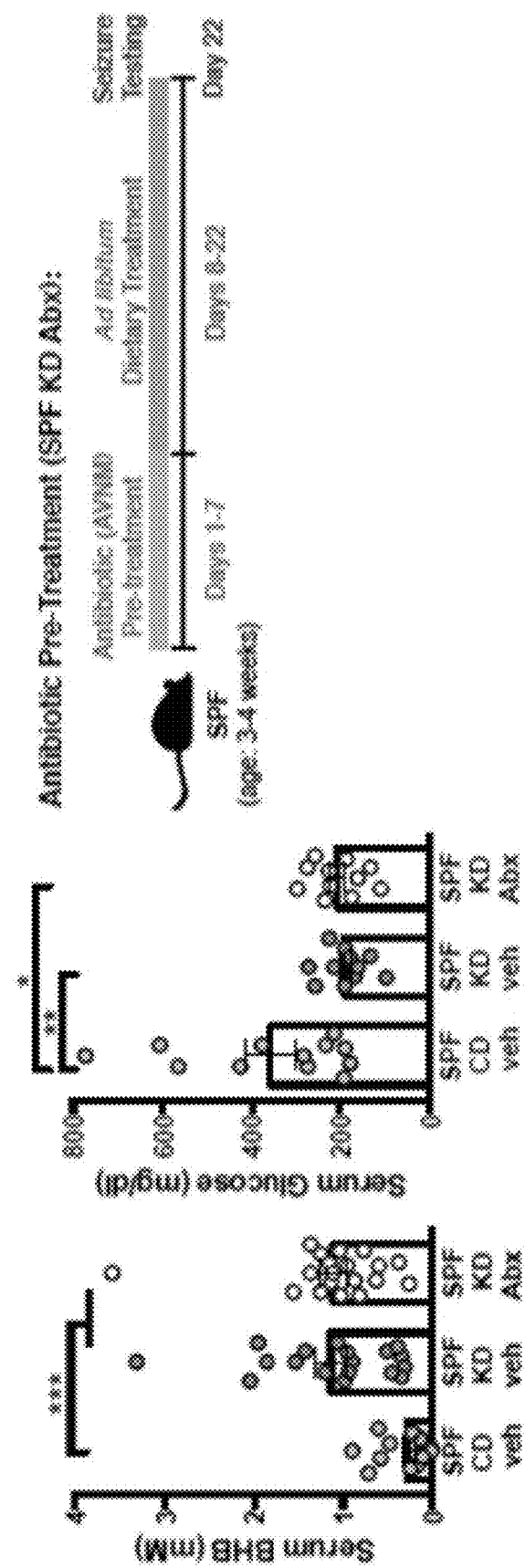

Compared to CD controls (SPF CD), SPF mice fed the KD (SPF KD) for 14 days exhibited increased seizure thresholds and altered microbiota (FIG. 3A and FIG. 1D). This was abrogated in GF mice (FIG. 3A) and Abx-treated SPF mice (FIG. 3C), indicating that the gut microbiota was required for KD-mediated increases in seizure protection. Conventionalization of GF mice with the SPF gut microbiota restored KD-associated seizure protection to levels seen in native SPF KD mice (FIG. 3A), which suggested that microbial mediation of KD seizure resistance was not dependent on pre-weaning microbiota colonization and that the microbiota actively mediated seizure protection by the KD. Notably, microbial modulation of KD-related seizure resistance did not correlate with changes in serum BHB or glucose levels (FIG. 3B and FIG. 3D). There were also no significant differences between groups in levels of intestinal, liver, or brain BHB. Overall, these data demonstrated that the gut microbiota was required for anti-seizure effects of the KD in the 6-Hz seizure model and further suggested that gut microbes modulated seizure susceptibility through mechanisms that do not involve alterations in BHB levels.

Figure 4A:
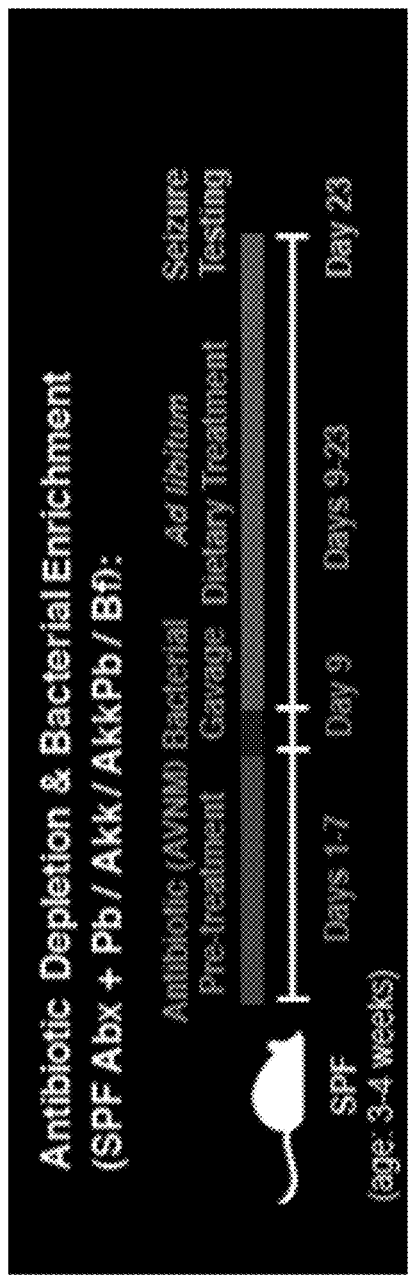
FIGS. 4A-B show that the KD-associated bacteria sufficiently mediated the anti-seizure effects of the ketogenic diet.
Figure 4A:
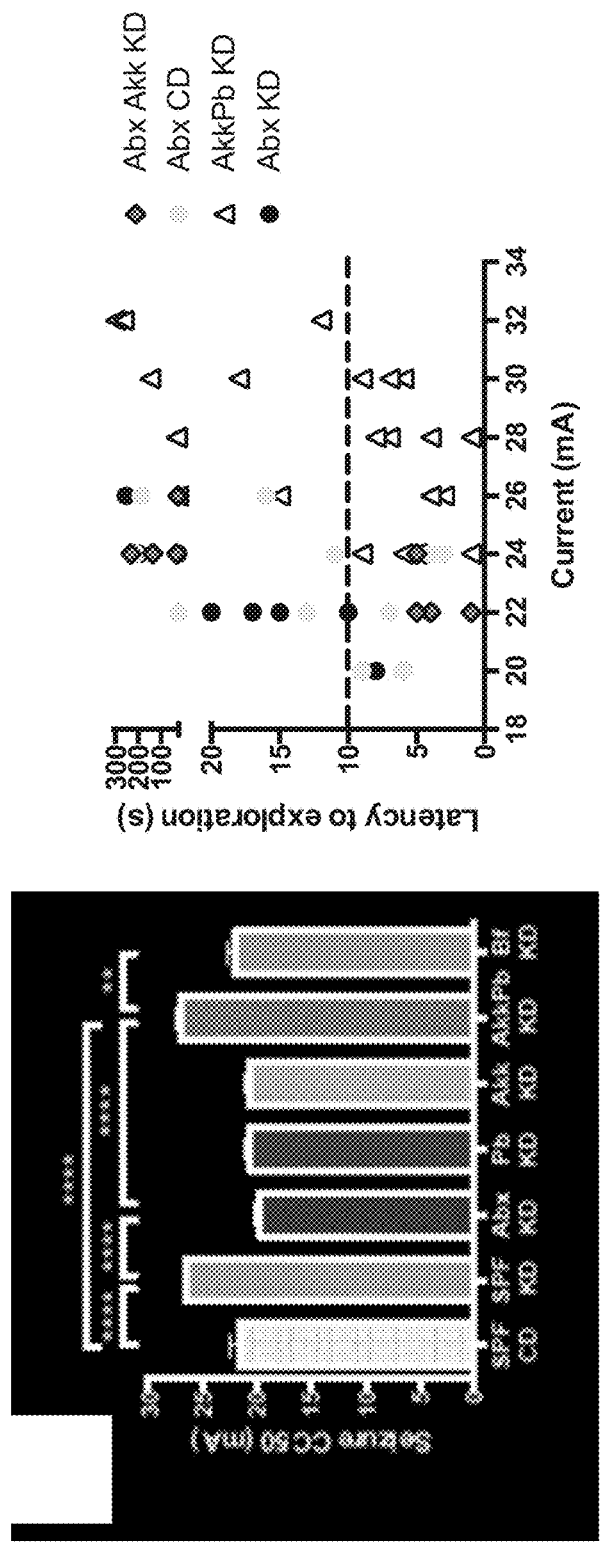
Figure 4B:
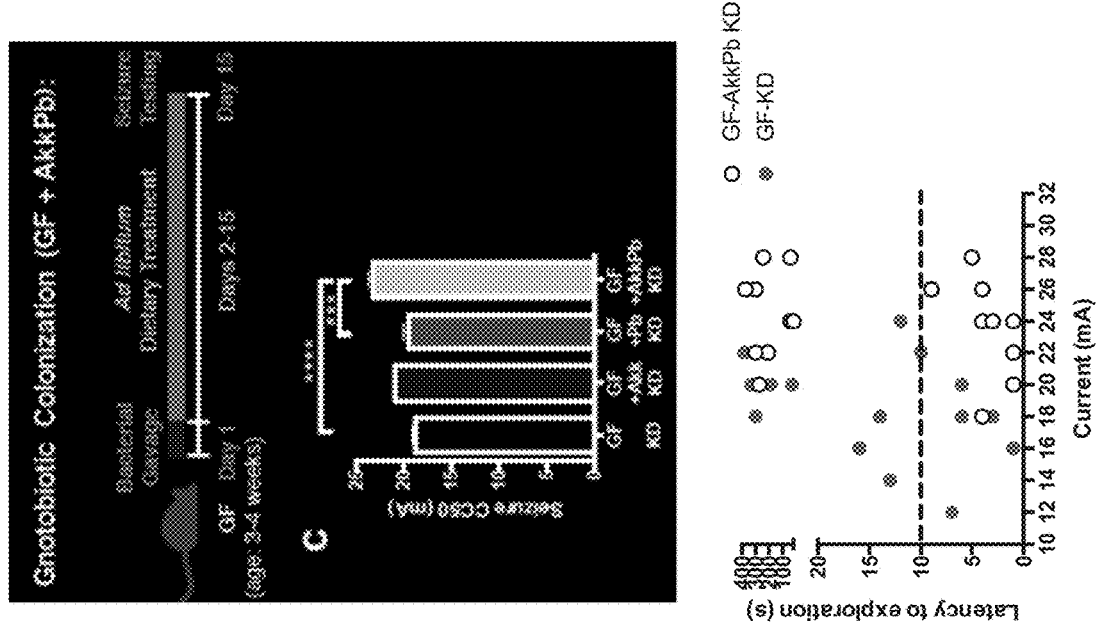

To determine whether specific bacterial taxa mediated seizure protection in response to the KD, Abx-treated SPF mice were colonized with select KD-associated bacteria, fed the KD and then tested for 6-Hz seizures (FIG. 4). Mice were gavaged with $10^9$ cfu bacteria: i) *A. muciniphila*; ii) 1:1 ratio of *Parabacteroides merdae* and *P. distasonis*, as representative intestinal *Parabacteroides* spp. from the human microbiota with highest homology to the *Parabacteroides* operational taxonomic unit reads that were enriched by the KD (FIG. 1D); or iii) 2.1:1 ratio of *A. muciniphila, P. merdae* and *P. distasonis*. At 14 days after gavage, 16S rDNA sequencing of colonic lumenal contents revealed that mice treated with *A. muciniphila* harbored 43.7±0.4% relative abundance of *A. muciniphila*. Mice gavaged with *Parabacteroides* spp. harbored 70.9±4.0% relative abundance, and mice gavaged with both taxa harbored 49.0±4.1% *A. muciniphila* and 22.5±5.4% *Parabacteroides*. Consistent with this, FISH processing of colonic sections from mice treated with *A. muciniphila* and *Parabacteroides* spp. exhibited increased hybridization of the *A. muciniphila* probe MUC1437 and the *Bacteroides* and *Parabacteroides* spp. probe BAC303, where the average distance from a BAC303-positive cell to the nearest MUC1437-positive cell is 0.64±0.09 microns. Both *A. muciniphila* and *Parabacteroides* spp. localized to the lumen of the mouse colon, not the mucosal space. There were no significant differences in weight, serum glucose levels, or enrichment of *A. muiciniphila* and *Parabacteroides* spp. across mice fed CD vs. KD. BHB was similarly induced in KD-fed groups, independent of colonization and seizure status. These data revealed that microbiota depletion by Abx treatment followed by oral gavage of exogenous bacteria resulted in their persistent intestinal enrichment by 14 days post-inoculation.

Treatment with the KD alone elevated seizure thresholds by 24.5% from 19.4±0.8 mA, in SPF CD mice, to 24.2±0.3 mA, in SPF KD mice. While co-administration of *A. muciniphila* and *Parabacteroides* spp. restored protection against 6-Hz seizures in Abx-treated mice fed the KD, raising thresholds by 36.0%, from 19.9±0.3 mA, in Abx KD mice, to 27.0±0.5 mA, in AkkPb KD mice (FIG. 4A). The seizure protective effect of bacterial enrichment was specific to *A. muciniphila* with *P. merdae*, as mice gavaged with *A. muciniphila* and *P. distasonis* exhibited no restoration of seizure protection. There was no significant increase in seizure threshold after enrichment of either *A. muciniphila* or *Parabacteroides* spp. alone (FIG. 4A), indicating that both were required for mediating the anti-seizure effects of the ketogenic diet. There also was no effect of treatment with *Bifidobacterium longum* (FIG. 4A), which was increased in CD-treated mice (FIG. 1F). Moreover, co-colonization of *A. muciniphila* and *Parabacteroides* spp. in GF mice promoted seizure protection in response to the KD, when compared to *Parabacteroides*-monocolonized or *A. muciniphila*-monocolonized in GF mice (FIG. 4C). Overall, these findings revealed that *A. muciniphila* and *Parabacteroides* spp. increased in response to the ketogenic diet and mediated its protective effect in the 6-Hz seizure model.

Figure 5A:
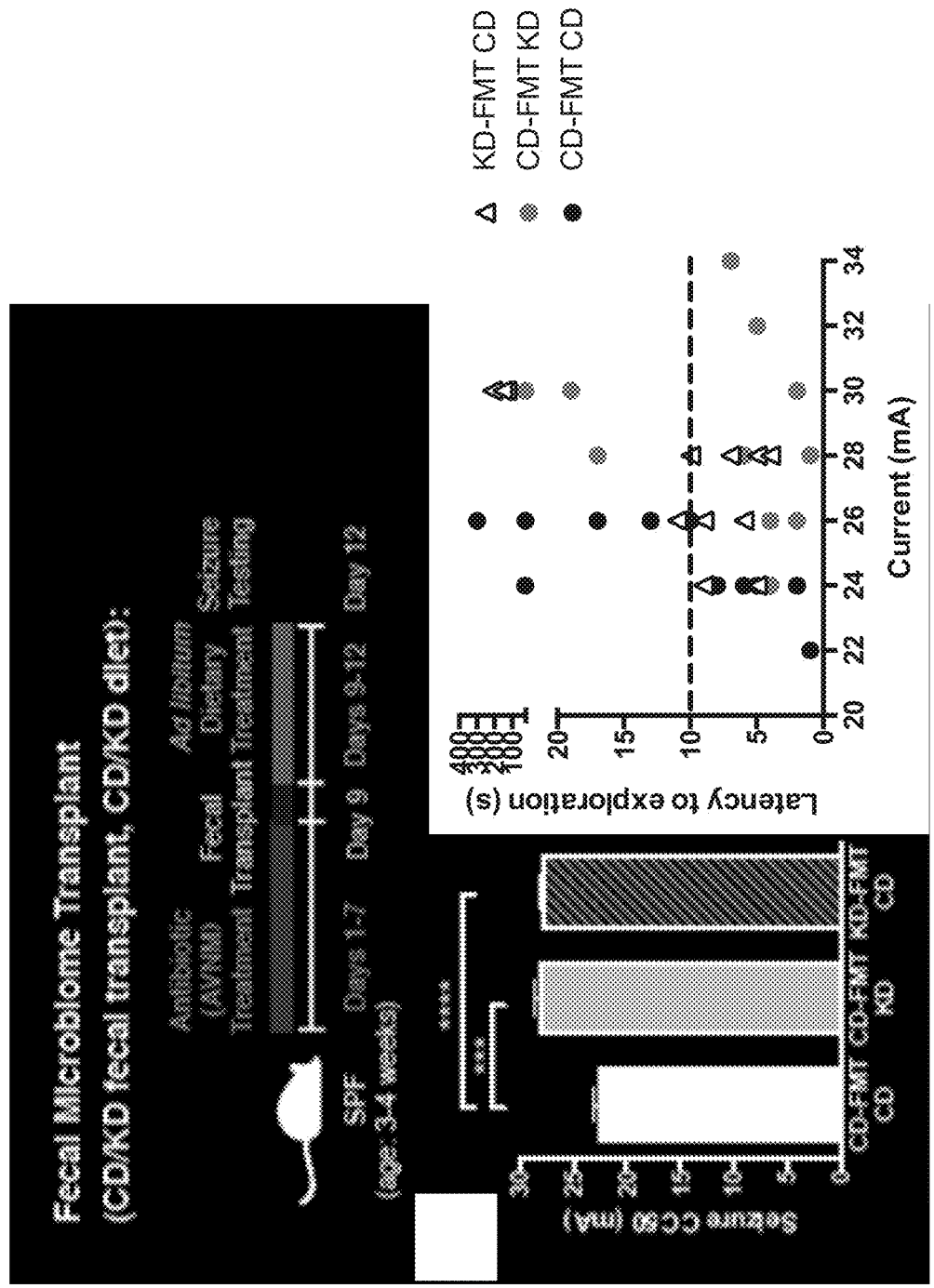
FIGS. 5A-C show KD-associated microbiota confer seizure protection in mice fed the control diet.
Figure 5B:
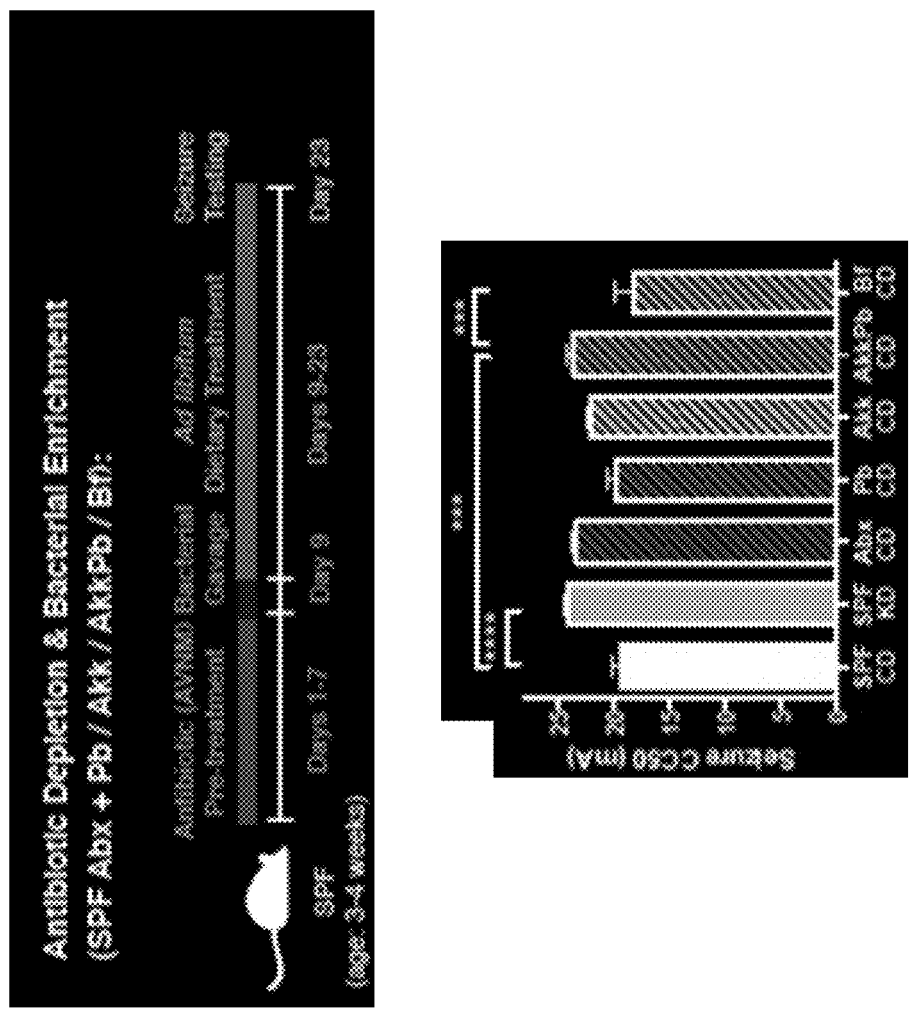
Figure 5C:
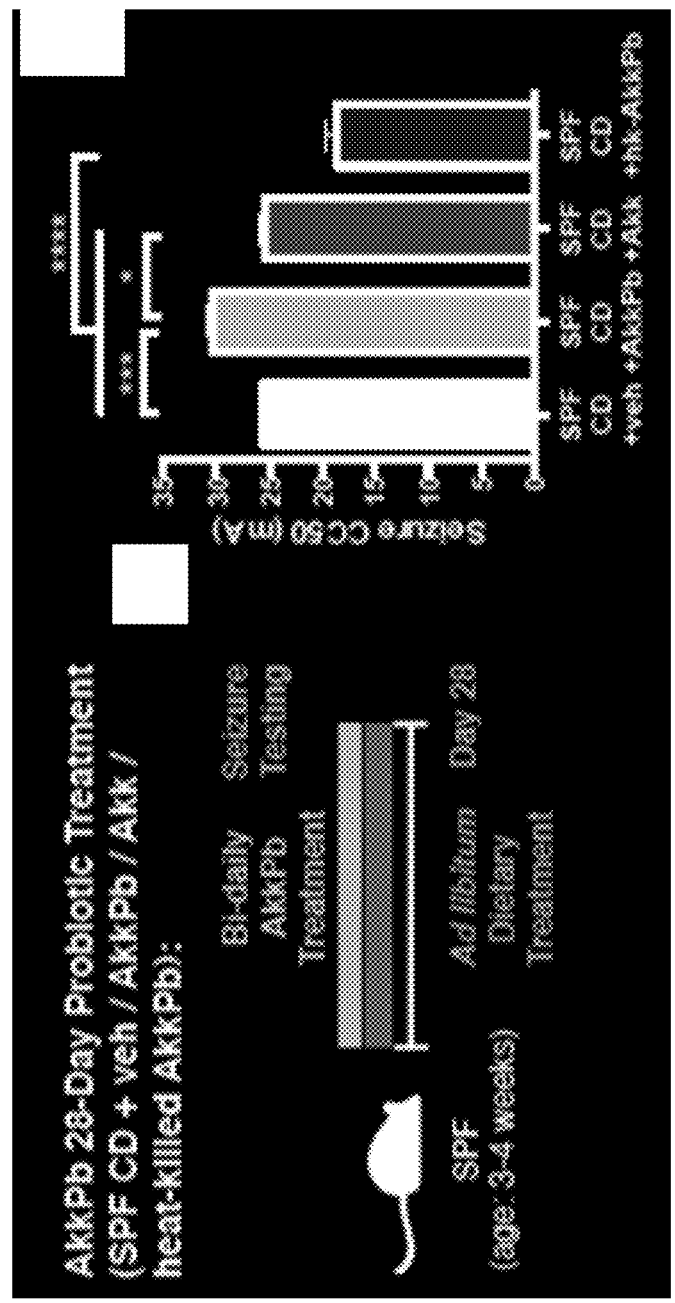
Figure 6A:
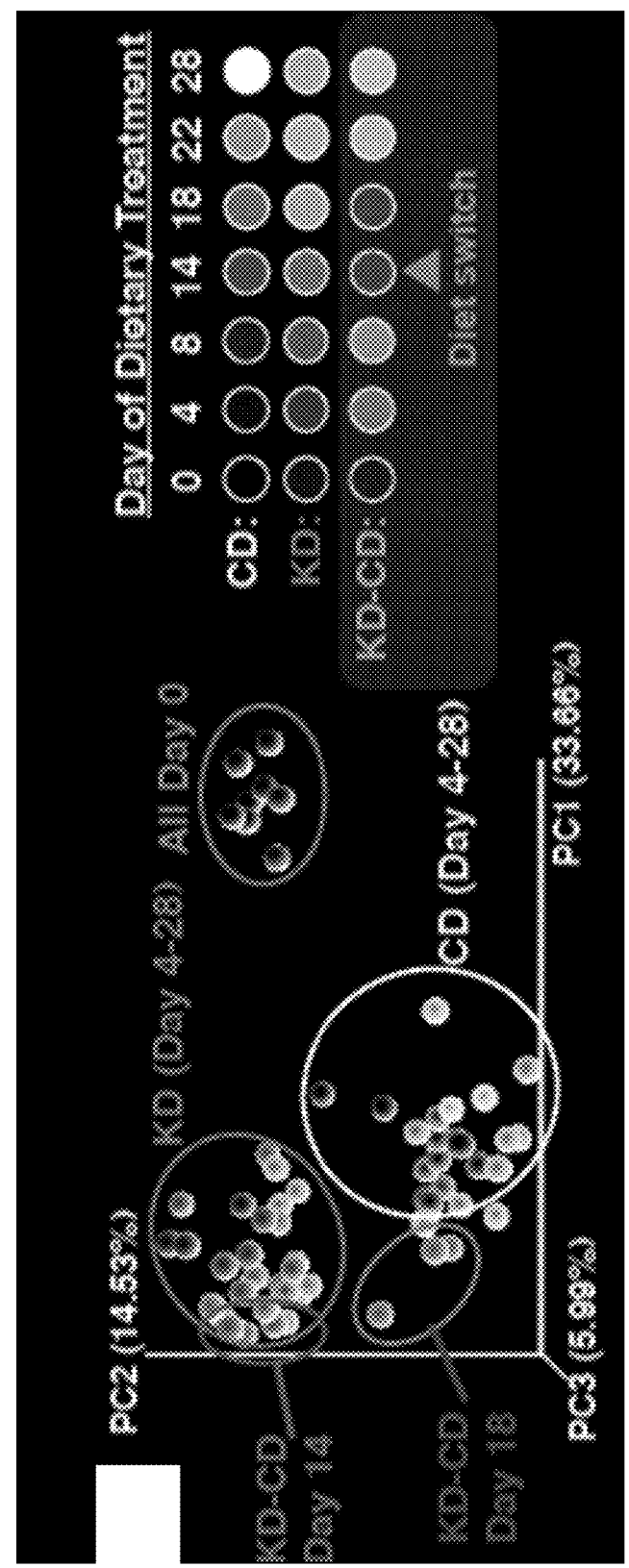
FIGS. 6A-D show the reversion of the KD microbiota and KD-associated seizure protection in response to the control diet.
Figure 6B:
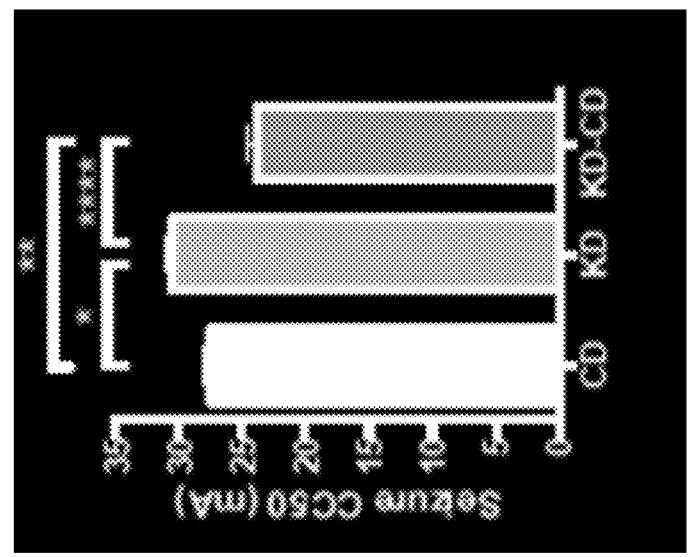
Figure 6C:
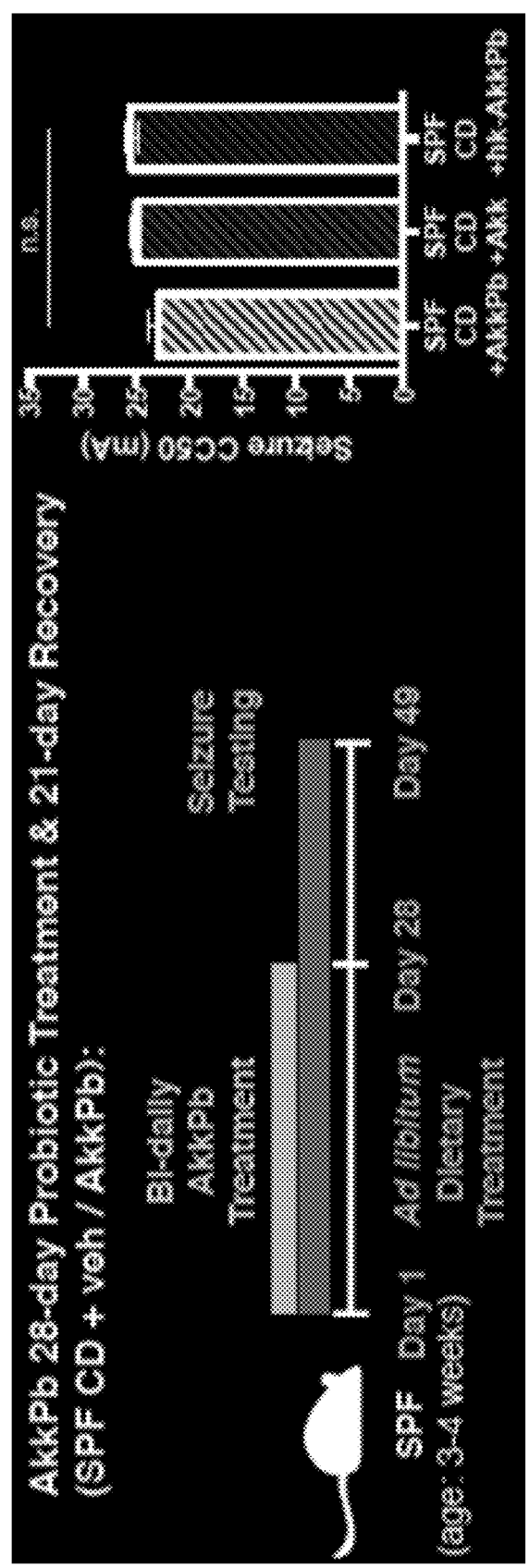
Figure 6D:
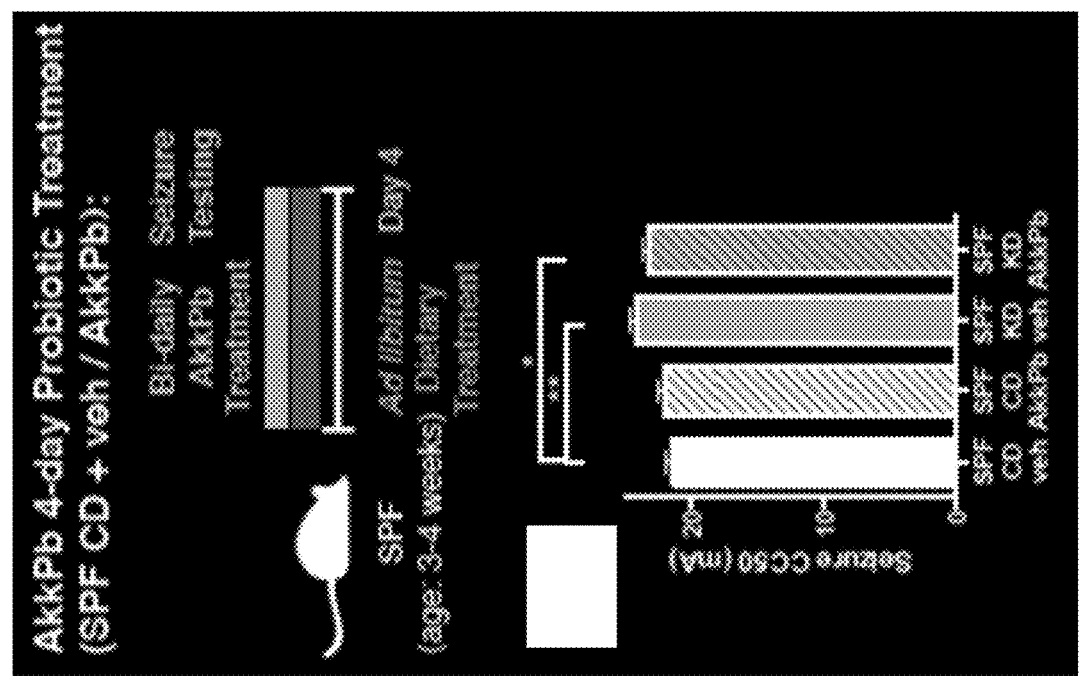

Example 4: The Gut Microbiota Sufficiently Confers Seizure Protection to Mice Fed the Control Diet To determine whether KD-associated gut microbes also conferred anti-seizure effects to mice fed the control diet, Abx-treated mice were transplanted with CD vs. KD microbiota from SPF mice, fed the CD or KD and tested for their susceptibility to 6-Hz seizures after 4 days of dietary treatment. Abx-treated mice were used to mimic clinical fecal transplant approaches that involve pre-treatment with Abx to deplete the native microbiota. Day 4 was selected based on i) the ability of the KD to induce significant microbiota changes by that time (FIG. 1D, FIG. 1F, and FIG. 5A) and ii) evidence that the KD microbiota exhibits incomplete reversion to CD profiles at 4 days after switching from KD to CD (FIG. 6A). Mice transplanted with a CD microbiota and fed KD for 4 days displayed increased seizure threshold compared to CD-fed controls (Figure 5A). Abx-treated mice transplanted with a KD microbiome but fed CD for 4 days exhibited seizure protection as well. This suggested that colonization with the KD microbiota raised seizure thresholds in mice fed CD. Notably, however, seizure protection was abrogated after complete reversion of the KD microbiota to CD profiles on day 28 (FIG. 6B), which suggested that persistent interactions between the KD microbiota, diet and neuronal activity were required. Similar anti-seizure effects were seen after enriching *A. muciniphila* and *Parabacteroides* spp. in Abx-treated SPF mice fed CD as compared to *Parabacteroides* spp., *A. muciniphila* or *B. longum* controls (FIG. 5B). However, increases in seizure threshold in SPF CD mice treated with Abx alone relative to SPF CD controls confounded interpretation of these results (FIG. 5B). To clarify this uncertainty, a bacterial treatment approach to investigate whether exogenous treatment with *A. muciniphila* and *Parabacteroides* spp. conferred anti-seizure effects in mice fed CD was applied. SPF CD mice were gavaged bi-daily for 28 days with $10^9$ cfu *A. muciniphila* and *Parabacteroides* spp. or with vehicle. This bacterial treatment increased seizure thresholds relative to vehicle-gavaged controls (FIG. 6C). Consistent with experiments on mice fed the ketogenic diet (FIG. 4), this seizure protection was not observed in animals treated with *A. muciniphila* alone, which revealed that co-administration of *A. muciniphila* and *Parabacteroides* spp. was required for seizure protection (FIG. 5C). Moreover, treatment with heat-killed bacteria decreased seizure thresholds compared to vehicle-treated controls, which suggested that viable bacteria were necessary for conferring anti-seizure effects and release of bacterial cell surface and/or intracellular factors promoted sensitivity to 6-Hz seizures. Persistent exposure to *A. muciniphila* and *Parabacteroides* spp. was required, as increases in seizure thresholds were lost after ceasing treatment for 21 days (FIG. 6C). In addition, seizure protection was not observed in mice treated for only 4 days (FIG. 6D), which suggested that long-term exposure was required. Taken together, these findings revealed that fecal transplant of the KD microbiota and bacterial treatment with the KD-associated taxa *A. muciniphila* and *Parabacteroides* spp. conferred protection against 6-Hz psychomotor seizures in mice fed the control diet.

Example 5: KD-Associated Bacteria Reduced Tonic-Clonic Seizures in Kcna1$^{-/-}$ Mice Epilepsy is a heterogeneous disorder with diverse clinical presentations. To determine whether the microbiota affected different seizure types, the roles for the gut microbiota in modulating generalized tonic-clonic seizures were tested in the Kcna1$^{-/-}$ mouse model for temporal lobe epilepsy and sudden unexpected death in epilepsy (SUDEP). Kcna1$^{-/-}$ mice harbor a null mutation in the voltage-gated potassium channel Kv1.1 alpha subunit, mimicking associations of human KCNA1 gene variants with epilepsy, episodic ataxia and SUDEP. Kcna1$^{-/-}$ mice develop severe spontaneous recurrent seizures, which are reduced 54% by the KD. Kcna1$^{-/-}$ SPF C3HeB/FeJ mice were treated with Abx or vehicle for 1 week, gavaged with vehicle or *A. miciniphila* and *Parabacteroides* spp., and fed KD or CD for 3 weeks. Seizure frequency and duration were recorded by EEG over 3 days, where electrographic seizures were identified based on characteristic epileptiform spike patterns consisting of 5 phases (FIG. 7C): A) low-frequency background, with low-voltage spiking, B) synchronized high-frequency, high-voltage spiking, C) high-frequency, low-voltage spiking, D) unsynchronized high-frequency, high-voltage spiking, and E) high-frequency, burst spiking. Furthermore, EEG seizure patterns were corroborated with stereotyped seizure behaviors identified by 5 stages. There were no significant differences in weight gain, food consumption between mice fed KD vs. CD. No differences in survival across groups were observed. Compared to CD-fed Kcna1$^{-/-}$ controls, KD-fed Kcna1$^{-/-}$ mice exhibited altered gut microbiota profiles (FIG. 7A), with increases in *A. muciniphila* and *Parabacteroides* spp. Notably, these changes were mild and not statistically significant compared to the KD-induced enrichment seen in Swiss Webster mice (FIG. 1F), which highlighted an effect of host genotype on baseline microbiota composition and responses to KD. Vehicle-treated Kcna1$^{-/-}$ mice exhibited seizures that lasted 15-180 seconds, with an average maximum spike amplitude of 490±26 uV (FIG. 7C). Decreases in seizure incidence and duration in KD-fed Kcna1$^{-/-}$ mice compared to CD-fed Kcna1$^{-/-}$ controls were observed (FIG. 7D), consistent with KD-mediated seizure protection as previously described. Kcna1$^{-/-}$ mice that were pre-treated with Abx to deplete the gut microbiota exhibited a significant increase in seizures per day and total seizure duration compared to vehicle-treated, KD-fed Kcna1$^{-/-}$ controls (FIG. 7D). There was no significant difference in spike frequency, interspike interval, and average duration per seizure which suggested a primary effect of Abx treatment and depletion of the gut microbiota on seizure occurrence. Moreover, colonization of Abx-treated Kcna1$^{-/-}$ mice with *A. muciniphila* and *Parabacteroides* spp. reduced seizure frequency and total duration of seizures toward levels seen in vehicle-treated, KD-fed Kcna1$^{-/-}$ controls (FIG. 7D). This suggested that treatment with *A. muciniphila* and *Parabacteroides* spp. similarly conferred seizure protection in mouse strains that have different baseline and diet-altered microbiota (in this case, C57Bl/6 vs. C3HeB/FeJ). Taken together, these findings supported the notion that select bacterial species from the indigenous gut microbiota mediated the anti-seizure effects of the KD across varied seizure types and models.

Example 6: Microbiota Modulated Gut, Serum, and Brain Metabolomes

Metabolomic profiling was used to identify candidate microbiota-dependent molecules in colonic lumenal contents and sera of SPF mice fed CD, and SPF, Abx-treated SPF, and *A. miciniphila-* and *Parabacteroides* spp.-enriched mice fed KD (FIG. 8A and FIG. 9A). Metabolomic profiles in colonic lumenal contents and sera discriminated seizure-protected (vehicle-treated SPF mice fed KD and *A. muciniphila* with *Parabacteroides* spp.-enriched mice fed KD) from seizure-susceptible (vehicle-treated SPF mice fed CD and Abx-treated SPF mice fed KD) groups, with a predictive accuracy of 94% for colonic lumenal metabolites and 87.5% for serum metabolites. The majority of metabolites that contributed highly to group discrimination were relevant to amino acid metabolism, including derivatives of lysine, tyrosine and threonine. In addition, widespread decreases in subsets of ketogenic gamma-glutamylated amino acids— gamma-glutamyl (GG)-leucine, GG-lysine, GG-threonine, GG-tryptophan and GG-tyrosine—in colonic lumenal contents (FIG. 8C) and sera (FIG. 8D) from seizure-protected compared to seizure-susceptible groups was observed. This suggested that the gut microbiota modulated gamma-glutamylation itself or selective metabolism of ketogenic GG-amino acids and that increased ketogenic GG-amino acids were associated with seizure susceptibility. Supporting this notion, imputed metagenomes predicted KD-associated alterations in bacterial genes relevant to amino acid metabolism. These data revealed significant effects of the gut microbiota on intestinal and systemic metabolomic responses to the KD, and further revealed an association between KD-induced seizure protection and microbiota-dependent alterations in levels of ketogenic GG-amino acids.

The brain relies on active import of essential amino acids to fuel neurotransmitter biosynthesis, and as such, is sensitive to fluctuations in peripheral amino acid bioavailability. GG-amino acids, in particular, are hypothesized to exhibit increased transport properties compared to non-gamma-glutamylated forms. Based on data that revealed diet- and microbiota-dependent alterations in serum ketogenic amino acids, links between amino acids importation and brain GABA levels, and prevailing theories that GABA contributed to the anti-seizure effects of the KD, bulk levels of GABA and glutamate in the hippocampus, a key region for seizure propagation, were examined. Hippocampal metabolite profiles distinguished samples for seizure-protected vs. seizure-susceptible mice. Hippocampal GABA/glutamate ratios are significantly increased in KD-fed SPF mice compared to CD-fed controls (FIG. 8D, left). These increases were abrogated in Abx-treated mice fed KD and restored after enrichment of Abx-treated mice with *A. muciniphila* and *Parabacteroides* spp. (FIG. 8D). Similar changes were seen for hippocampal levels of glutamine, a precursor of glutamate and GABA (FIG. 8D, right). Overall, these results revealed diet- and microbiota-dependent regulation in the bioavailability of glutamine, as well as a preferential increase in hippocampal GABA levels relative to glutamate in seizure-protected mice.

Example 7: Bacterial Gamma-Glutamylation Impacted Seizure Susceptibility

Based on the finding that essential ketogenic GG-amino acids were reduced in colonic lumen and serum of seizure-protected vs. seizure-susceptible experimental groups, it was hypothesized that microbiota-dependent restriction of ketogenic GG-amino acids is important for mediating the anti-seizure effects of the KD. Gamma-glutamylated forms of amino acids were generated by transpeptidation of GG moieties from glutathione onto amino acids. To determine whether gamma-glutamylation of amino acids impacts seizure susceptibility, SPF CD mice were gavaged for 3 days with GGsTop, a selective irreversible inhibitor of GGT. SPF CD mice treated with GGsTop exhibited increases in seizure thresholds toward levels seen in SPF KD mice (FIG. 10A). Similarly, EEG recordings of CD-fed SPF Kcna1−/− mice treated with GGsTop displayed a significant decrease in seizures per day (FIG. 7E). This demonstrated that peripheral inhibition of gamma-glutamylation and restriction of GG-amino acids promoted seizure protection, consistent with observed metabolomic decreases of ketogenic GG-amino acids in colonic lumenal content and sera from seizure-protected groups compared to seizure-susceptible controls. To determine whether restriction of amino acids, rather than catabolism of glutathione, was necessary for the anti-seizure effects of the KD microbiota, KD-fed *A. miciniphila* and *Parabacteroides* spp.-enriched mice were supplemented by bi-daily intraperitoneal injection for 3 days with combined leucine, lysine, threonine, tryptophan and tyrosine, and then tested for 6-Hz seizures. Physiologically-relevant concentrations of amino acids were calculated based on serum metabolomic data, such that dosages for each restored blood levels to that seen in vehicle-treated SPF CD controls. Elevating systemic levels of ketogenic amino acids decreased seizure thresholds to levels seen in vehicle-treated SPF CD controls (FIG. 10B). This suggested that restriction of peripheral ketogenic amino acids was necessary for mediating microbiota- and KD-dependent increases in seizure resistance.

Both host cells and particular bacterial species exhibit GGT activity. To gain insight into whether the KD and interactions between *A. muciniphila* and *Parabacteroides* spp. suppressed bacterial gamma-glutamylation in vivo, GGT activity was measured in fecal samples collected from SPF or *A. muciniphila* and *Parabacteroides* spp.-enriched mice fed the CD or KD. Feeding SPF mice with KD decreased fecal GGT activity compared to CD controls (FIG. 10C) Similar reduction in fecal GGT activity was seen after enriching *A. muciniphila* and *Parabacteroides* spp. in CD-fed mice. Moreover, enriching *A. miciniphila* and *Parabacteroides* spp. and feeding with KD further decreased fecal GGT activity relative to that seen in SPF KD and SPF CD mice. Exposing all fecal samples to the GGT inhibitor GGsTop eliminated the detected signals, confirming that the measurements reflected GGT activity. Consistent with this, treatment of CD-fed SPF mice with *A. muciniphila* and *Parabacteroides* spp. decreased fecal GGT activity relative to vehicle-treated controls and mice treated with heat-killed bacteria (FIG. 10D). Overall, these data revealed that enriching for or exogenous treatment with *A. muciniphila* and *Parabacteroides* spp. reduced fecal GGT activity, which could explain the low levels of colonic and serum GG-amino acids observed in seizure-protected mice.

To explore whether bacterial gamma-glutamylation was affected by interactions between *A. muciniphila* and *Parabacteroides* spp., GGT activity in bacteria grown in an in vitro cross-feeding system was measured. When *A. muciniphila* was embedded in a CD- or KD-based agar, and *P. merdae* was overlaid in M9 minimal media over the agar, both bacteria exhibited enhanced growth (FIG. 10E and FIG. 10F), which suggested that *A. muciniphila* liberated soluble factors to enable *P. merdae* growth and in turn *P. merdae* enhanced *A. muciniphila* growth. Pilot experiments revealed no growth of *A. muciniphila* in M9 media when overlaid on *P. merdae* embedded in KD or CD agar, which suggested that *A. muciniphila* cannot rely solely on cross-feeding from *P. merdae* to persist.

*P. merdae* exhibited high GGT activity that was eliminated by the addition of *A. muciniphila* embedded in CD or KD agar (FIG. 10G and FIG. 10H). To determine whether reduction of GGT activity in *P. merdae* promoted *A. muciniphila* growth, *P. merdae* was pre-treated with vehicle or GGsTop to pharmacologically inhibit GGT activity prior to testing in the cross-feeding assay. *A. muciniphila* exposed to *P. merdae* that was pre-treated with GGsTop exhibited increased growth at 24 hours after incubation as compared to *A. muciniphila* exposed to vehicle-treated *P. merdae* (FIG. 11B). Taken together, these findings suggested that *A. muciniphila* was capable of metabolizing components from the KD and CD diet to support *P. merdae* growth, and that the cooperative interaction reduced GGT activity. In turn, reductions in GGT activity in *P. merdae* promotes *A. muciniphila* growth. This was consistent with the finding that enrichment of *A. muciniphila* and *Parabacteroides* spp. reduced fecal GGT activity, colonic lumenal GG-amino acids and serum GG-amino acids. This demonstrated that amino acid restriction was required for seizure protection and that inhibition of GGT promoted seizure protection. This aligned with previous studies linking GGT activity to altered seizure severity. In a study of 75 epileptic patients, high serum GGT activity was observed in 84.5% of the patients compared to controls. In a rat seizure model, GGT activity was increased after 5 consecutive daily electroshock deliveries. Decreases in various peripheral amino acids are associated with KD-mediated seizure suppression in animals and humans.

Based on the data herein and existing literature on roles for peripheral amino acids as substrates for brain neurotransmitter biosynthesis, it was hypothesized that bacterial regulation of GG-amino acids altered brain import of amino acids that fuel GABA/glutamate metabolism (FIG. 8). Notably, several gut bacteria are reported to synthesize GABA de novo; however, circulating GABA exhibits limited transport across the blood-brain barrier. In addition, changes in the gut microbiota have been associated with alterations in brain GABA levels, but the molecular mechanisms involved remain unclear. Additional studies are needed to determine whether GG-amino acids influence brain transport of amino acids and local synthesis of glutamate versus GABA.

Overall, this study demonstrated a novel role for select KD-associated gut bacteria—*A. muciniphila* and *Parabacteroides* spp.—in mediating and conferring seizure protection in mouse models for refractory epilepsy. Increases in *A. muciniphila* were similarly observed during fasting in humans, hamsters, squirrels, and pythons, and in response to caloric restriction and high polyunsaturated fat diets in mice. *A. muciniphila* and *Parabacteroides* spp. are also positively associated with increased ketosis and the ketogenic diet in humans. The data herein reveals a likely pathway whereby the KD promoted select microbe-microbe interactions that reduced host levels of ketogenic GG-amino acids and elevated the total bioavailability of GABA relative to glutamate in the hippocampus. Pharmacological inhibition of gamma-glutamylation increased seizure thresholds, which suggested that reduced GGT activity was important for mediating the anti-seizure effects of the KD-associated gut microbiota in mice. Notably, given that lack of bacterial GGT activity in the GF condition was associated with seizure susceptibility, it is likely that *A. muciniphila* and *Parabacteroides* spp. contributed functions in addition to suppression of GGT activity that may also contribute to seizure protection.

INCORPORATION BY REFERENCE

All publications and patents mentioned herein are hereby incorporated by reference in their entirety as if each individual publication or patent was specifically and individually indicated to be incorporated by reference. In case of conflict, the present application, including any definitions herein, will control.

EQUIVALENTS

While specific embodiments of the subject invention have been discussed, the above specification is illustrative and not restrictive. Many variations of the invention will become apparent to those skilled in the art upon review of this specification and the claims below. The full scope of the invention should be determined by reference to the claims, along with their full scope of equivalents, and the specification, along with such variations.

We claim:

1. A method of treating a seizure in a mammalian subject, comprising administering to the subject a therapeutically effective amount of a pharmaceutical composition comprising:
   (a) live *Akkermansia muciniphila* bacteria; and
   (b) live *Parabacteroides merdae* bacteria,
   wherein the *Akkermansia muciniphila* bacteria and the *Parabacteroides merdae* bacteria are present in a ratio of 2:1.

2. The method of claim 1, wherein the composition is a dry composition.

3. The method of claim 1, wherein the composition is formulated for oral delivery.

4. The method of claim 1, wherein the composition is formulated into a pill, tablet, or capsule.

5. The method of claim 4, wherein the tablet or the capsule is a time-released tablet or capsule.

6. The method of claim 4, wherein the tablet or the capsule is enterically coated.

7. The method of claim 1, wherein the composition comprises other probiotic agents or nutrients which promote the growth of beneficial probiotic bacteria.

8. The method of claim 1, wherein the composition comprises a pharmaceutically acceptable carrier.

9. The method of claim 8, wherein the pharmaceutically acceptable carrier is selected from micro-crystalline cellulose (MCC), trehalose, maltodextrin, rice flour, magnesium stearate, inositol, dextrose, and sucrose.

10. The method of claim 1, wherein the subject has epilepsy.

11. The method of claim 1, comprising
   (i) depleting the gut microbiota of the subject; and
   (ii) administering to the subject a therapeutically effective amount of a pharmaceutical composition comprising live *Akkermansia muciniphila* bacteria and live *Parabacteroides merdae* bacteria, wherein the *Akkermansia muciniphila* bacteria and the *Parabacteroides merdae* bacteria are present in a ratio of 2:1.

12. The method of claim 11, wherein the subject is given antibiotics to deplete the subject's gut microbiota.

* * * * *